United States Patent
Li et al.

(10) Patent No.: US 9,696,254 B2
(45) Date of Patent: Jul. 4, 2017

(54) DEVICE AND METHOD FOR ALIGNMENT

(71) Applicant: Taiwan Biophotonic Corporation, Zhubei (TW)

(72) Inventors: Yu-Tang Li, Zhubei (TW); Chang-Sheng Chu, Zhubei (TW); Pei-Cheng Ho, Zhubei (TW); Kuan-Jui Ho, Zhubei (TW); Shuang-Chao Chung, Zhubei (TW); Chih-Hsun Fan, Zhubei (TW); Jyh-Chern Chen, Zhubei (TW)

(73) Assignee: Taiwan Biophotonic Corporation, Hsinchu (TW)

( * ) Notice: Subject to any disclaimer, the term of this patent is extended or adjusted under 35 U.S.C. 154(b) by 0 days.

(21) Appl. No.: 15/093,749

(22) Filed: Apr. 8, 2016

(65) Prior Publication Data
US 2016/0298956 A1 Oct. 13, 2016

Related U.S. Application Data

(60) Provisional application No. 62/146,381, filed on Apr. 12, 2015.

(51) Int. Cl.
| | | |
|---|---|---|
| G01B 11/00 | (2006.01) | |
| G01N 21/21 | (2006.01) | |
| A61B 5/1455 | (2006.01) | |
| G01B 11/27 | (2006.01) | |
| G01N 33/483 | (2006.01) | |
| A61B 3/10 | (2006.01) | |
| A61B 3/15 | (2006.01) | |

(52) U.S. Cl.
CPC ............... *G01N 21/21* (2013.01); *A61B 3/10* (2013.01); *A61B 3/152* (2013.01); *A61B 5/1455* (2013.01); *G01B 11/272* (2013.01); *G01N 33/483* (2013.01); *G01N 2201/0633* (2013.01); *G01N 2201/0683* (2013.01); *G01N 2201/126* (2013.01)

(58) Field of Classification Search
CPC ................. G01N 21/21; G01N 33/483; G01N 2201/0633; A61B 3/152; A61B 3/145; A61B 3/10; A61B 3/103; A61B 3/165; G01B 11/272; G02B 26/06
USPC ................... 356/399–401, 237.2–237.6, 364
See application file for complete search history.

(56) References Cited

U.S. PATENT DOCUMENTS 3,036,568 A * 5/1962 Stark ..................... A61B 3/112
351/205
3,832,890 A * 9/1974 Grolman ................ A61B 3/165
600/401
(Continued)

FOREIGN PATENT DOCUMENTS

JP P2000-23920 A 1/2000
JP P2007-196069 A 8/2007
(Continued)

*Primary Examiner* — Tarifur Chowdhury
*Assistant Examiner* — Isiaka Akanbi
(74) *Attorney, Agent, or Firm* — Steven Reiss

(57) ABSTRACT

The present disclosure generally relates to a device and a method for alignment. The alignment device provides optical architecture to align the alignment device to an analyte and measure the optical properties of an analyte. The method for alignment provides steps for aligning an optical measurement device to an analyte.

18 Claims, 32 Drawing Sheets

(56) References Cited

U.S. PATENT DOCUMENTS

| | | | | |
|---|---|---|---|---|
| 4,944,303 | A * | 7/1990 | Katsuragi | A61B 3/165 600/401 |
| 4,991,584 | A * | 2/1991 | Kobayashi | A61B 3/145 351/211 |
| 5,076,274 | A * | 12/1991 | Matsumoto | A61B 3/165 600/401 |
| 5,206,672 | A * | 4/1993 | Rowe | A61B 3/103 351/205 |
| 6,666,857 | B2 * | 12/2003 | Smith | A61F 9/008 606/11 |
| 6,733,129 | B2 | 5/2004 | Masaki | |
| 8,363,783 | B2 | 1/2013 | Gertner et al. | |
| 8,690,328 | B1 * | 4/2014 | Chong | A61B 3/14 351/205 |
| 2007/0121071 | A1 * | 5/2007 | Jackson | A61B 3/0033 351/246 |
| 2008/0165322 | A1 | 7/2008 | Su et al. | |
| 2014/0086533 | A1 | 3/2014 | Gold et al. | |
| 2014/0171765 | A1 | 6/2014 | Li et al. | |

FOREIGN PATENT DOCUMENTS

| | | |
|---|---|---|
| JP | P2012-183123 A | 9/2012 |
| JP | P2014-108136 A | 6/2014 |
| JP | P2014-150857 A | 8/2014 |
| TW | 201411769 A | 3/2014 |
| WO | 2014/084231 A1 | 6/2014 |
| WO | 2014/134324 A1 | 9/2014 |
| WO | 2014/158263 A1 | 10/2014 |

* cited by examiner

DEVICE AND METHOD FOR ALIGNMENT

FIELD

The subject matter herein generally relates to an optical device and a method for alignment.

BACKGROUND

Non-invasive measurement of biochemical parameters is influential to the modern healthcare quality. An accurate, efficient, safe measurement is desperately desired by human beings. However, poor alignment of an optical measurement device to an analyte leads to inaccuracy and inconsistency of optical measurement.

Although current technology has paid a lot of effort to perform good alignment, complicated alignment device is not suitable for user compliance and usually the alignment is not consist with the measurement region. Therefore, the present disclosure includes a device and method for optical alignment to increase the accuracy and consistency of the measurement. The person having ordinary skill in the art may appreciate the present disclosure and the examples are described but not limited in the specification without departing from the scope of the disclosure.

BRIEF DESCRIPTION OF THE DRAWINGS

Implementations of the present technology will now be described, by way of example only, with reference to the attached figures.

DETAILED DESCRIPTION

Figure 1A:
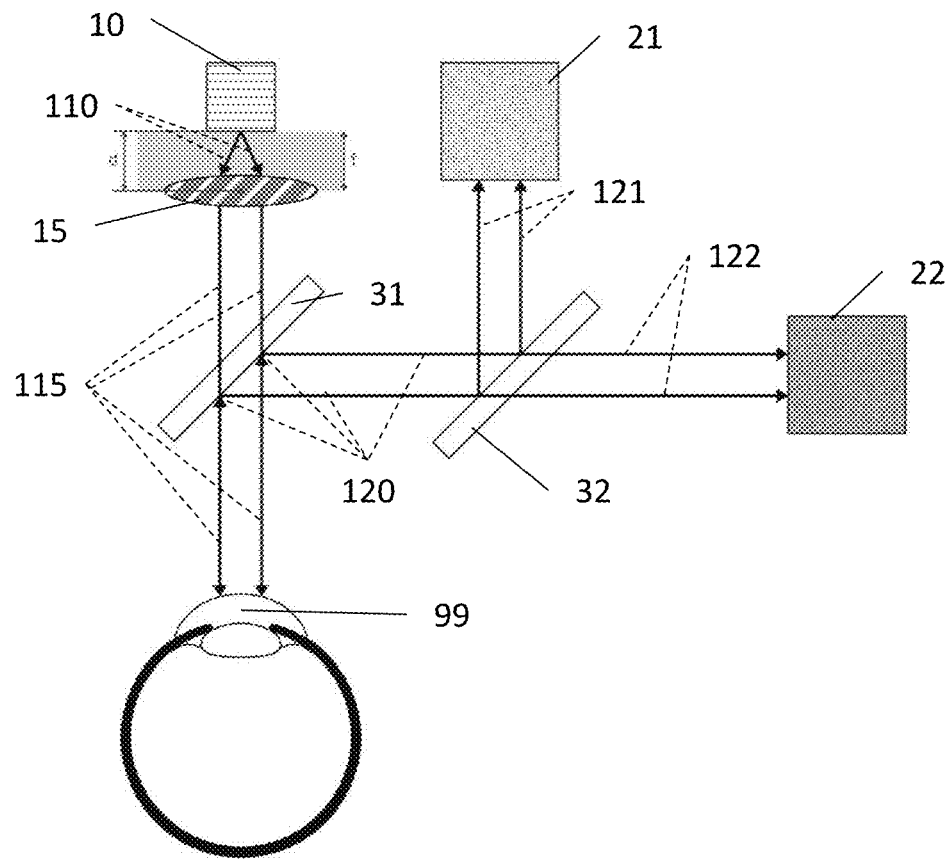
FIG. 1A shows an example of an optical measurement module, wherein the collimated light beam is a parallel light beam.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "light beam" is defined as a directional projection of light energy, and is not necessarily limited to the optical path directly connected between two optical components. For example, a light beam may come from a light source to a photodetector, with or without passing through a beam splitter between the light source and the photodetector. The direction or the optical properties of a light beam may be changed when passing through an optical component. The term "collimate" is defined to narrow the beam divergence of a light beam or to converge a light beam, and is not necessarily limited to make the light beam parallel. The term "substantially" is defined to be essentially conforming to the particular dimension, shape or other word that substantially modifies, such that the component need not be exact. The term "comprising" means "including, but not necessarily limited to"; it specifically indicates open-ended inclusion or membership in a so-described combination, group, series and the like.

In the present disclosure, an optical measurement module is configured to detect the optical properties of an analyte. The optical measurement module may be integrated in a device or a system to have further applications. An optical measurement device is configured to measure the existence or the concentration of a target molecule or the composition of the chemical compounds. The analyte may be a mixture of chemical compounds or a part of a biological sample in vivo (for example, blood, skin, eye, or mucosa) or ex vivo (for example, blood, biopsy sample, urine or feces). The optical measurement module or the optical measurement device is capable of detecting the optical properties of the chemical compounds in variable depth of the biological sample. For example, the analyte may be cornea, sclera, aqueous humor, lens, vitreous humor, or retina. The existence or the concentration of a specific biochemical compound in an analyte (e.g., glucose, lactate, or hemoglobin) may be measured by the combination of interested optical properties. In addition, some disease status of a subject may also be further determined in vivo or ex vivo, such as keratoconjunctivitis sicca in eye, or dysplasia in a tissue biopsy. The interested optical properties are absorbance, refractive index, polarization, fluorescence, and inelastic scattering.

The optical measurement module may comprise a light source, a collimator, a first beam splitter, a second beam splitter, a first light receiving module, and a second light receiving module. Moreover, the distance between the light source and the collimator may be configured for the specific applications. With a collimated light beam focused at the limited area, most acquired information is extracted from the desired region of the analyte. On the other hand, the collimated light beam may be projected as a parallel light beam to acquire the average information of the defined area of the object, so that the present disclosure may greatly reduce regional variation, especially if the object is a heterogeneous constitution or a non-static fluid. The details of the examples will be described below.

A light source is a light emitting element or a composition of multiple light emitting elements. The light source may be a monochromatic light source or a polychromatic light source. The light source may be embodied as a laser diode, a light emitting diode, or an organic light emitting diode. In certain examples, the light source may have plural laser diodes, light emitting diodes, or organic light emitting diodes and each of the light emitting element may have different wavelength or polarization. The polychromatic light source may be an incandescent light source or a calibrated white light source. Within the present disclosure, the light is electromagnetic radiation with the wavelength from ultraviolet, visible light, to infrared regions. The light source may further comprise an optical component to modify the optical properties of emitted light beam. The optical component may be a linear polarizer, a dichroic filter, or a collimator.

A collimator is an optical component that narrows the emitting angle of light beams. A collimator has a focal length (denoted as f) defined by the distance from the focal plane to the optical center of the collimator. When a light source is placed at the focus, the emitting light beams is guided as a set of parallel light beams with a limited cross sectional area corresponding to the structure of the collimator; when a light source is placed closer to the focus, the emitting light beams is guided as a set of light beams with a constrained emitting angle; when a light source is placed further to the focus, the emitting light beams is guided as a set of light beams converging at a limited distance from the collimator. The examples of a collimator may be a converging lens, a condenser lens, a convex lens, a plano-convex lens, a plano-concave lens, a double convex lens, or a biconcave lens. Furthermore, the optical measurement module or the optical measurement device may comprise a mechanical component so that the distance between the light source and the collimator may be adjustable.

A beam splitter is capable of splitting a light beam into two directions according to the optical properties, such as wavelength, polarization, or dividing neutrally into a certain proportion. Also, the beam splitter is capable of directing a part of a light beam to a predetermined direction via transmission or reflection. The construction of a beam splitter may be embodied as a prism, a lens, or a mirror. For example, a neutral beam splitter decomposes the light beams without changing the spectral division; a dichroic beam splitter separates the light beams spectrally. A beam splitter may also be a polarizing beam splitter, which divides the light into beams of different polarization, such as Wollaston prism.

A light receiving module is configured to detect the light beam with a specific optical property, and the light receiving module comprises at least a photodetector. The photodetector may be embodied as a photodiode, a phototransistor, a photoresistor, a photomultiplier, or a metal oxide semiconductor (MOS). Also, a light receiving module may comprise a linear array or a two dimensional array of plural photodetectors as described above, or a linear array or a two dimensional array of charge coupled device (CCD) or complementary metal oxide semiconductor (CMOS). The light receiving module may comprise an image sensor, for example, a CCD image sensor, a CMOS image sensor or a camera. Depending on the examples, a light receiving module may further comprises an optical component, which is configured to isolate or modulate the light beams with specific optical properties so that the photodetector is able to transduce the energy of the light beams into electrical signals. The optical component in a light receiving module may be a filter, a polarizer, or a dispersion element, and may be embodied as a lens, a prism, a mirror or a grating. A light receiving module may further comprise a mechanical rotator or a faraday rotator for measuring optical rotation. It is contemplated that a light receiving module may further comprises amplifiers and/or the analogue to digital converter for the ease of signal processing. In present disclosure, the first light receiving module and the second light receiving module may be placed interchangeably because transmission and refection of the second beam splitter may be functionally equivalent.

An optical measurement module may comprise a light source, a collimator, a first beam splitter, a second beam splitter, a first light receiving module, and a second light receiving module. Here, the distance (denoted as d) between the light source and the collimator is determined by the reference of the focal length (denoted as f) of the collimator. An original light beam emitted from the light source is converged by the collimator into a collimated light beam. The collimated light beam may be a parallel light beam or a focused light beam according to the distance between the light source and the collimator.

In FIG. 1A, an optical measurement module may comprise a light source 10, a collimator 15, a first beam splitter 31, a second beam splitter 32, a first light receiving module 21, and a second light receiving module 22, wherein the distance between the light source 10 and the collimator 15 is the focal length of the collimator 15, and the collimated light beam 115 is a parallel light beam.

Generally, a light beam is a directional projection of light energy propagating along a designated light path. For clarity of description, the definition of light beam is described according to the directional light path between the corresponding components. An original light beam 110 is the light beam emitted by the light source 10 traveling to the collimator 15, and the original light beam may have certain optical properties, such as narrow wavelength, spectral wavelength, coherence, polarization, or any combination of the optical properties. An original light beam 110 becomes a collimated light beam 115 after passing through a collimator 15. A collimated light beam 115 may travels from the collimator 15 through the first beam splitter 31 reaching to an analyte 99. A measurement light beam 120 is the light beam remaining on the light path after interaction with an analyte 99, where the interaction may be refraction, reflection, diffusion, absorption, fluorescence emission, optical rotation, elastic scattering, and/or inelastic scattering. A part of measurement light beam 120 is delivered from the analyte 99 via the first beam splitter 31 to the second beam splitter 32 and then divided into a first detection light beam 121 and a second detection light beam 122 by the second beam splitter 32. A first detection light beam 121 traveled from the second beam splitter 32 is detected by a first light receiving module 21, and a second detection light beam 122 traveled from the second beam splitter 32 is detected by a second light receiving module 22.

In one example, the first light receiving module is configured to measure the axis of the polarization plane of the light beam, or the optical rotation of an analyte 99. The optical rotation, or optical activity, of a material is referred to as the ability to rotate the orientation of linearly polarized light. The light source 10 may emit a polarized light beam, wherein the light source 10 may be a linear polarized light source or an unpolarized light source with a polarizer. The first light receiving module 21 may further comprise a polarizer, and the optical rotation may be estimated by Malus' law with the power intensity detected by the photodetector and the axial angle between the polarized light and the polarizer. In the same example, the second light receiving module 22 may be configured to measure other optical properties of an analyte 99, such as the refractive index, absorbance, fluorescence, or inelastic scattering. First, the second light receiving module 22 may be configured to measure refractive index of an analyte 99. With a single photodetector in the second light receiving module 22, the refractive index of an analyte 99 can be calculated from the power intensity detected by the photodetector by Fresnel equation or can be calculated from the power intensity change due to light path shift. With an array of photodetectors, the refractive index of an analyte 99 can be calculated from the light path shift detected by the array of photodetectors by Snell's law or prism equation. With the information of polarization and refractive index of an analyte 99, the existence or concentration of glucose or lactic acid may be estimated. Second, the second light receiving module 22 may be configured to measure absorbance of an analyte 99. With a single photodetector in the second light receiving module 22, the absorbance at specific wavelength of an analyte 99 can be calculated from the power intensity detected by the photodetector by Beer-Lambert's law. With an array of photodetectors and a dispersion element, and further with a calibrated spectral light source 10, the absorbance spectrum of an analyte 99 can be calculated from the power intensity distribution detected by the array of photodetectors. With the information of optical rotation and absorbance of an analyte 99, the existence or concentration of glucose, lactic acid, hemoglobin, oxyhemoglobin, urea, alcohol, or cancer cell may be estimated. Third, the second light receiving module 22 may be configured to measure the fluorescence of an analyte 99. With a single photodetector and a long pass filter (or a notch filter) in the second light receiving module 22 and an appropriate narrow wavelength light source 10, the fluorescence intensity of an analyte 99 can be calculated from the power intensity detected by the photodetector. With an array of photodetectors and a dispersion element in the second light receiving module 22 and an appropriate narrow wavelength light source 10, the fluorescence emission spectrum of an analyte 99 can be calculated from the power intensity distribution detected by the array of photodetectors. With the information of optical rotation and fluorescence of an analyte 99, the existence or concentration of glucose or lactic acid may be estimated. Fourth, the second light receiving module 22 may be configured to measure the inelastic scattering of an analyte 99. With an array of photodetectors and a dispersion element, and an appropriate narrow wavelength light source 10, the Raman spectrum of an analyte 99 can be calculated from the power intensity distribution detected by the array of photodetectors. With the information of optical rotation and inelastic scattering of an analyte 99, the existence or concentration of glucose or lactic acid may be estimated.

In one example, the first light receiving module 21 is configured to measure the refractive index of an analyte 99. Here, the light source 10 may be a monochromatic light source 10. With single photodetector in the first light receiving module 21, the refractive index of an analyte 99 can be calculated from the power intensity detected by the photodetector by Fresnel equation. With an array of photodetectors, the refractive index of an analyte 99 can be calculated from the light path shift detected by the array of photodetectors by Snell's law or prism equation. In the same example, the second light receiving module 22 may be configured to measure other optical properties of an analyte 99, such as the absorbance, fluorescence, or inelastic scattering. First, the second light receiving module 22 may be configured to measure absorbance of an analyte 99. With single photodetector in the second light receiving module 22, the absorbance at specific wavelength of an analyte 99 can be calculated from the power intensity detected by the photodetector by Beer-Lambert's law. With an array of photodetectors and a dispersion element, and further with a calibrated spectral light source 10, the absorbance spectrum of an analyte 99 can be calculated from the power intensity distribution detected by the array of photodetectors. With the information of refractive index and absorbance of an analyte 99, the existence or concentration of glucose, lactic acid, hemoglobin, oxyhemoglobin, urea, alcohol, or cancer cell may be estimated. Second, the second light receiving module 22 may be configured to measure the fluorescence of an analyte 99. With single photodetector and a filter in the second light receiving module 22 and an appropriate narrow wavelength light source 10, the fluorescence intensity of an analyte 99 can be calculated from the power intensity detected by the photodetector. With an array of photodetectors and a dispersion element in the second light receiving module 22 and an appropriate narrow wavelength light source 10, the fluorescence emission spectrum of an analyte 99 can be calculated from the power intensity distribution detected by the array of photodetectors. With the information of refractive index and fluorescence of an analyte 99, the existence or concentration of glucose, lactic acid, hemoglobin, oxyhemoglobin, urea, alcohol, or cancer cell may be estimated. Third, the second light receiving module 22 may be configured to measure the inelastic scattering of an analyte 99. With an array of photodetectors and a dispersion element, and an appropriate narrow wavelength light source 10, the Raman spectrum of an analyte 99 can be calculated from the power intensity distribution detected by the array of photodetectors. With the information of refractive index and inelastic scattering of an analyte 99, the existence or concentration of glucose, lactic acid, hemoglobin, oxyhemoglobin, urea, alcohol, or cancer cell may be estimated.

In one example, the first light receiving module 21 is configured to measure the absorbance of an analyte 99. Here, the light source 10 may be a narrow bandwidth light source or a calibrated spectral light source. With single photodetector in the first light receiving module 21, the absorbance of an analyte 99 can be calculated from the power intensity detected by the photodetector by Beer-Lambert's law. With an array of photodetectors and a dispersion element, and further with a calibrated spectral light source 10, the absorbance spectrum of an analyte 99 can be calculated from the power intensity distribution detected by the array of photodetectors. In the same example, the second light receiving module 22 may be configured to measure other optical properties of an analyte 99, such as the fluorescence, or inelastic scattering. For one thing, the second light receiving module 22 may be configured to measure the fluorescence of an analyte 99. With single photodetector and a filter in the second light receiving module 22 and an appropriate narrow wavelength light source 10, the fluorescence intensity of an analyte 99 can be calculated from the power intensity detected by the photodetector. With an array of photodetectors and a dispersion element in the second light receiving module 22 and an appropriate narrow wavelength light source 10, the fluorescence emission spectrum of an analyte 99 can be calculated from the power intensity distribution detected by the array of photodetectors. With the information of absorbance and fluorescence of an analyte 99, the existence or concentration of glucose, lactic acid, hemoglobin, oxyhemoglobin, urea, alcohol, or cancer cell may be estimated. Besides, the second light receiving module 22 may be configured to measure the inelastic scattering of an analyte 99. With an array of photodetectors and a dispersion element, and an appropriate narrow wavelength light source 10, the Raman spectrum of an analyte 99 can be calculated from the power intensity distribution detected by the array of photodetectors. With the information of absorbance and inelastic scattering of an analyte 99, the existence or concentration of glucose, lactic acid, hemoglobin, oxyhemoglobin, urea, alcohol, or cancer cell may be estimated.

In one example, the first light receiving module 21 is configured to measure the fluorescence of an analyte 99. Here, the light source 10 may be a narrow bandwidth light source. With single photodetector and a filter in the first light receiving module 21 and an appropriate narrow wavelength light source 10, the fluorescence intensity of an analyte 99 can be calculated from the power intensity detected by the photodetector. With an array of photodetectors and a dispersion element in the second light receiving module 22 and an appropriate narrow wavelength light source 10, the fluorescence emission spectrum of an analyte 99 can be calculated from the power intensity distribution detected by the array of photodetectors. The second light receiving module 22 may be configured to measure the inelastic scattering of an analyte 99. With an array of photodetectors and a dispersion element, and an appropriate narrow wavelength light source 10, the Raman spectrum of an analyte 99 can be calculated from the power intensity distribution detected by the array of photodetectors. With the information of fluorescence and inelastic scattering of an analyte 99, the existence or concentration of glucose or lactic acid may be estimated.

Figure 1B:
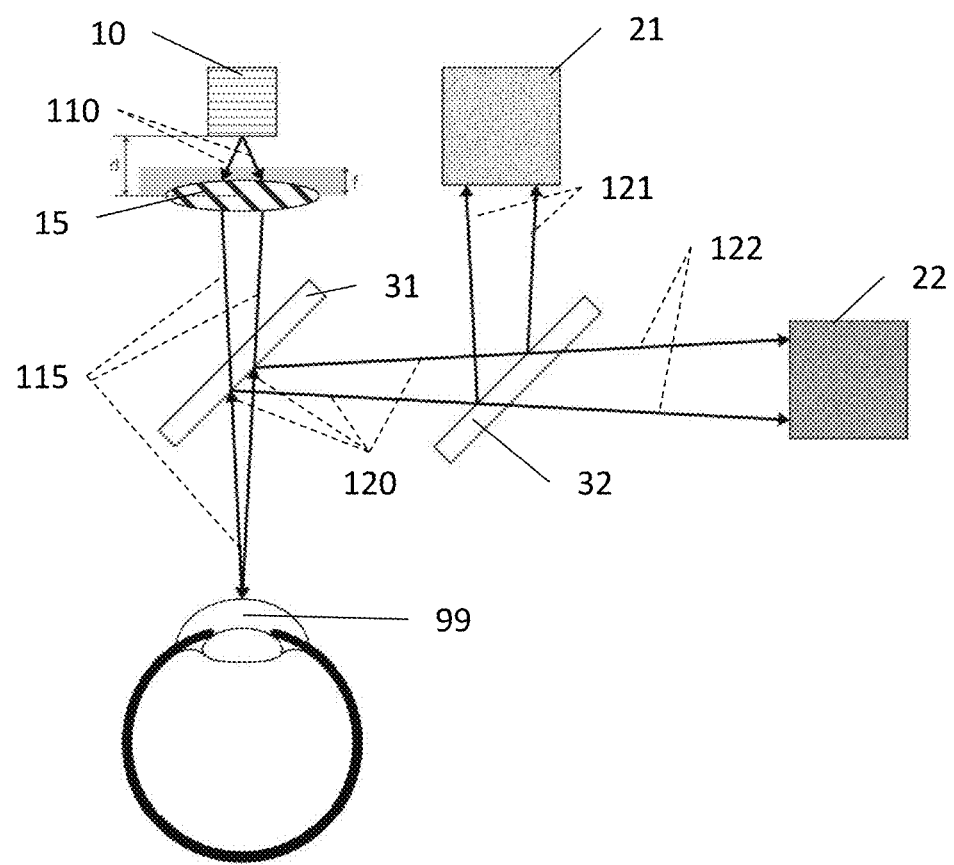
FIG. 1B shows an example of an optical measurement module, wherein the collimated light beam is a focused light beam.

In FIG. 1B, an optical measurement module may comprise a light source 10, a collimator 15, a first beam splitter 31, a second beam splitter 32, a first light receiving module 21, a second light receiving module 22, wherein the distance between the light source 10 and the collimator 15 is larger than the focal length of the collimator 15, and the collimated light beam 115 is a focused light beam.

Figure 1C:
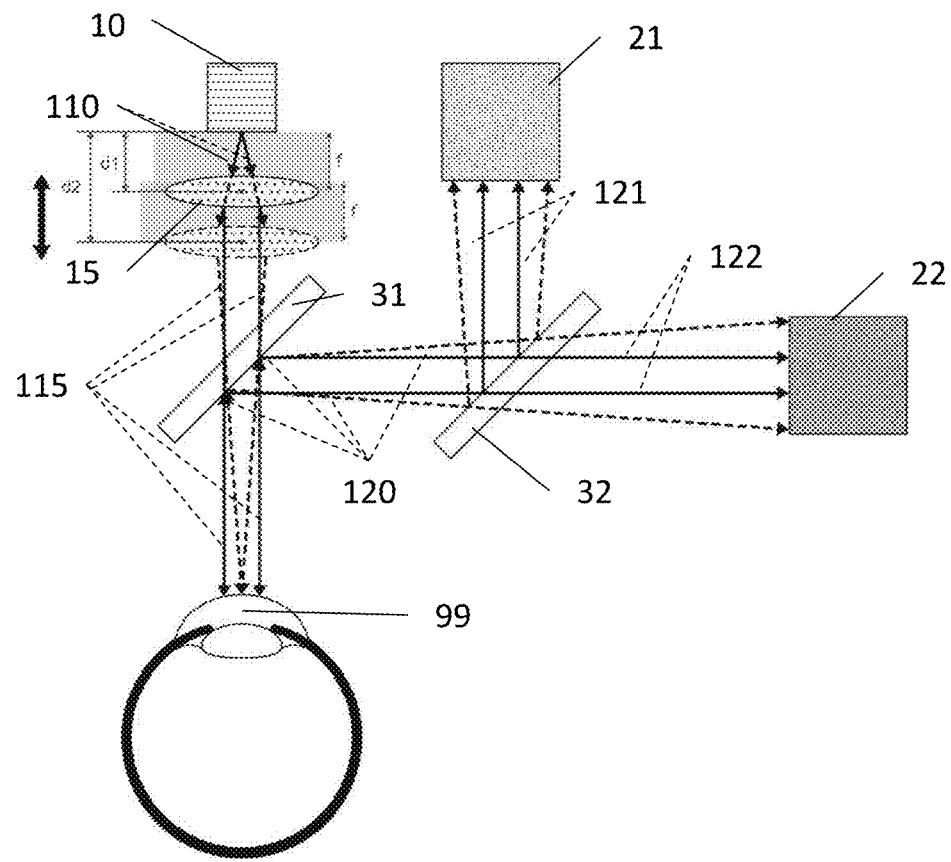
FIG. 1C shows an example of an optical measurement module, wherein the distance between the light source and the collimator is adjustable.

In FIG. 1C, an optical measurement module may comprise a light source 10, a collimator 15, a first beam splitter 31, a second beam splitter 32, a first light receiving module 21, a second light receiving module 22, and a tunable mechanical module. The distance between the light source 10 and the collimator 15 is adjustable. The tunable mechanical module is configured to adjust the distance between the collimator 15 and the light source 10, and the distance may be adjusted as same as the focal length of the collimator 15 to project a parallel light beam or may be adjusted as larger than the focal length of the collimator 15 to project a focused light beam.

Figure 2A:
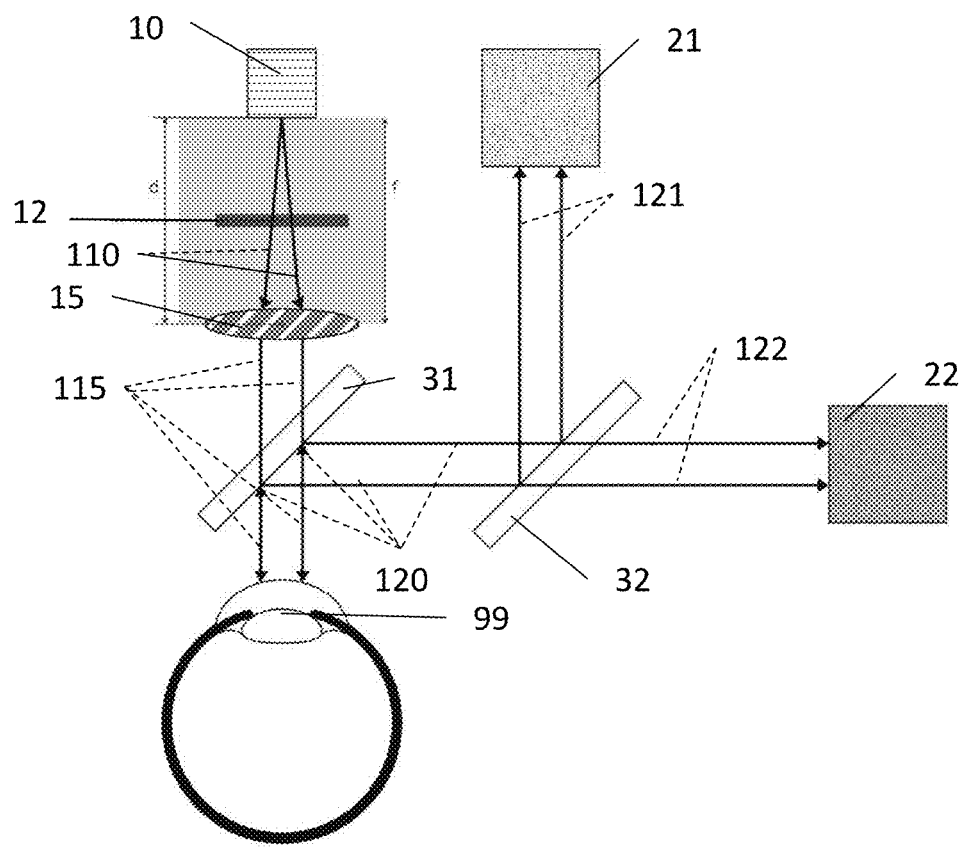
FIG. 2A shows a bandpass filter between the light source and the collimator.

An optical measurement module may further comprise an optical component. The optical component is configured between the light source 10 and the collimator 15 to specify the optical properties of the original light beam 110, such as intensity, bandwidth, and/or polarization, and the accuracy and consistency may therefore be improved. In one example as shown in FIG. 2A, the optical component may be embodied as a band pass filter 12 between the light source 10 and the collimator 15. The bandwidth of the light source 10 may be not sufficiently sharp for some specific purposes of measurement, such as fluorescence. With a band pass filter, the full width at half maximum (FWHM) of the emitted light is further narrowed down and closer to monochromatic light. Therefore, the original light beam may be monochromatic light.

Figure 2B:
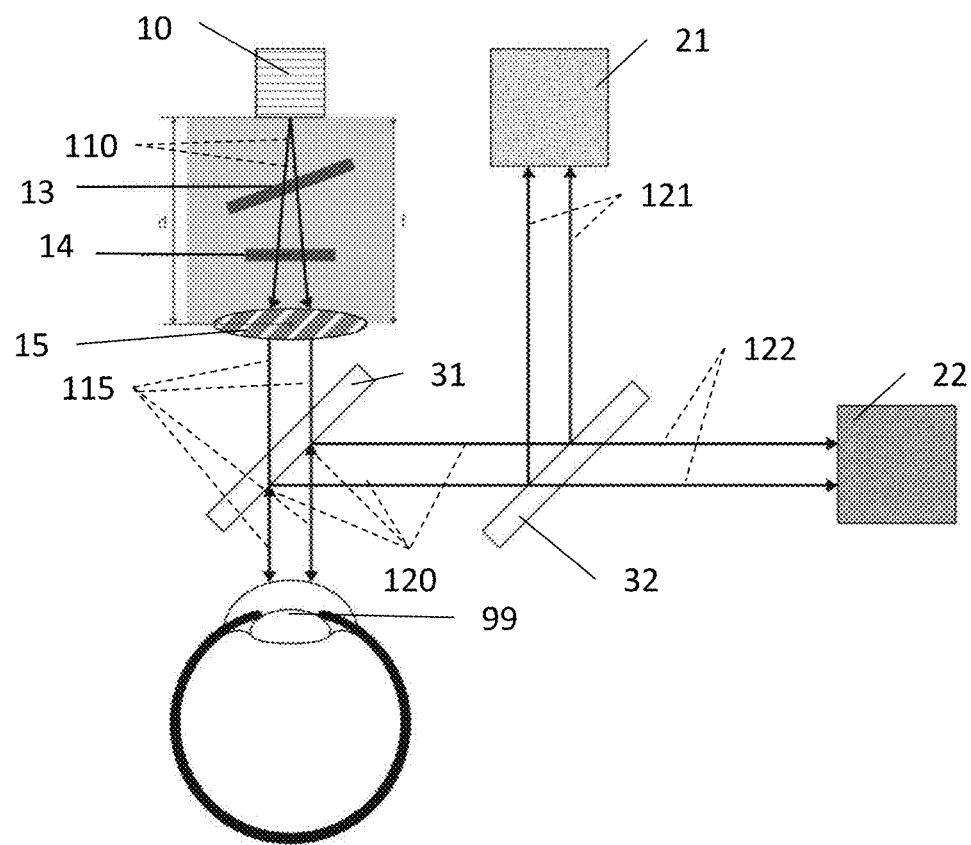
FIG. 2B shows a linear polarizer and a quarter waveplate between the light source and the collimator.

In FIG. 2B, an optical measurement module may comprise a quarter waveplate 14. Usually, the collimator 15 inevitably reflects part of the original light beam 110, which interferes with the original light beam 110, so this feedback noise greatly decreases the signal noise ratio of the measurement result. To solve the problem, a quarter waveplate 14 is placed between said polarizer and the collimator 15 to convert the original light beam 110 as circular polarized. In this way, the reflected part of circular polarized light beam is not able to interfere the original light beam 110, and thus reduce light source 10 output noise. Therefore, the original light beam may be a polarized light. Furthermore, for multiple modalities of measurement, restrict requirements of the original light beam 110 is critical, and both FWHM and DOP is needed to be control to meet accuracy and consistency. For example, the original light beam may be monochromatic polarized light.

Figure 2C:
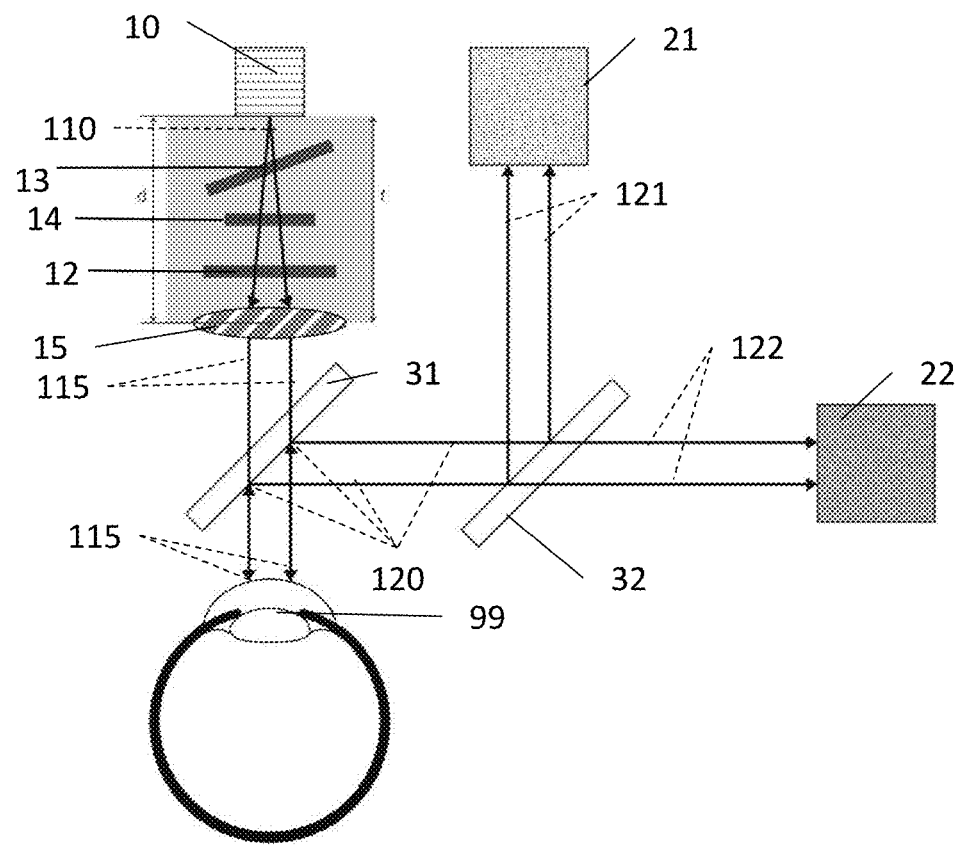
FIG. 2C shows a bandpass filter, a linear polarizer and a quarter waveplate between the light source and the collimator.

In FIG. 2C, the optical component may be embodied as a linear polarizer. The linear polarizer may increase the degree of the polarization (DOP) so that the signal noise ratio of the measurement of optical rotation can be highly increased. The linear polarizer 13 is placed between the light source 10 and the collimator 15; a quarter waveplate 14 is placed between the linear polarizer and the collimator 15; and a band pass filter 12 may be placed between the light source 10 and the linear polarizer 13 or between the quarter waveplate 14 and the collimator 15. Therefore, the original light beam may be monochromatic polarized light.

An optical measurement device may comprise the optical measurement module, a memory, a microprocessor, a power source, and a housing. The microprocessor is an integrated circuit configured to receive, process, and transmit the electrical signals to and from other electronic components, such as light source, photodetector, memory, image sensor, display, spatial sensor, or an actuator module. The memory is configured to store the data processed by the microprocessor or the preset programs. The memory may be a volatile memory, such as random access memory (RAM) or a non-volatile memory, such as a flash memory. At the age of present disclosure, a microprocessor and a memory may be integrated as a system in package (SiP) for cost-effectiveness and functionality. Similarly, a microprocessor may comprise an amplifier and/or an analogue-to-digital converter (ADC). A power source is configured to provide sufficient electrical energy to drive all the electronic components, and it may be embodied as a lithium based battery or a power supply draining and converting the alternating current from a power socket. The housing is configured to accommodate the components of the optical measurement device for better integration and application.

Figure 3A:
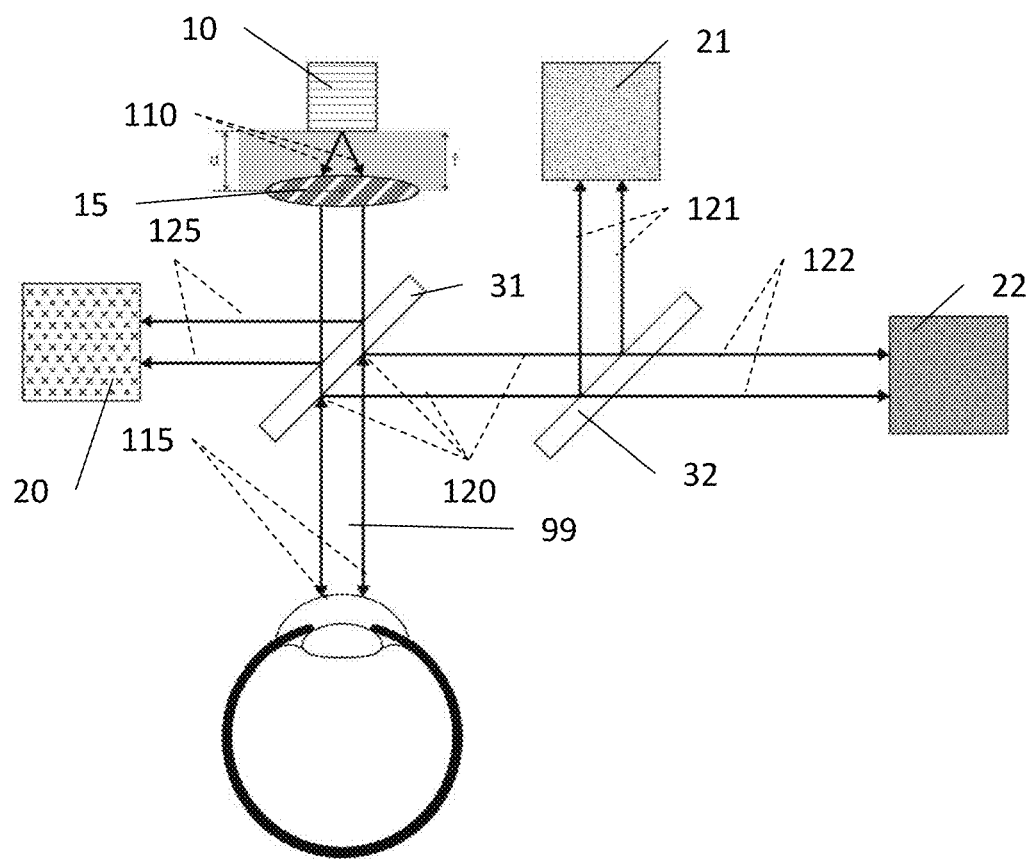
FIG. 3A illustrates an example of the present disclosure with a zeroth light receiving module and the associated light path.

In FIG. 3A, an optical measurement device may further comprise a zeroth light receiving module 20, which is configured to measure the power intensity of the feedback light beam 125 and further estimate collimated light beam 115 emitted from the light source 10. In the example of a laser diode as a light source 10, the laser power control is an important issue for safety and preventing damage to analytes 99. Thus, the connection of the optical measurement module, microprocessor 41 and the light source 10 is necessary to work with tight cooperation.

An original light beam 110 is converged as a collimated light beam 115 by a collimator 15. A collimated light beam 115 may travels from a collimator 15 through the first beam splitter 31 reaching to an analyte 99. A part of the collimated light beam 115 is guided by the first beam splitter 31 as a feedback light beam 125, which travels from the first beam splitter 31 to the zeroth light receiving module 20. Consequently, the feedback light beam 125 is transduced into electrical signals by the zeroth light receiving module 20. Also, a part of the measurement light beam is delivered from the analyte 99 via the first beam splitter 31 to the second beam splitter 32 and then divided into a first detection light beam and a second detection light beam by the second beam splitter 32. A first detection light beam traveled from the second beam splitter 32 is detected by a first light receiving module 21, and a second detection light beam traveled from the second beam splitter 32 is detected by a second light receiving module 22.

Figure 3B:
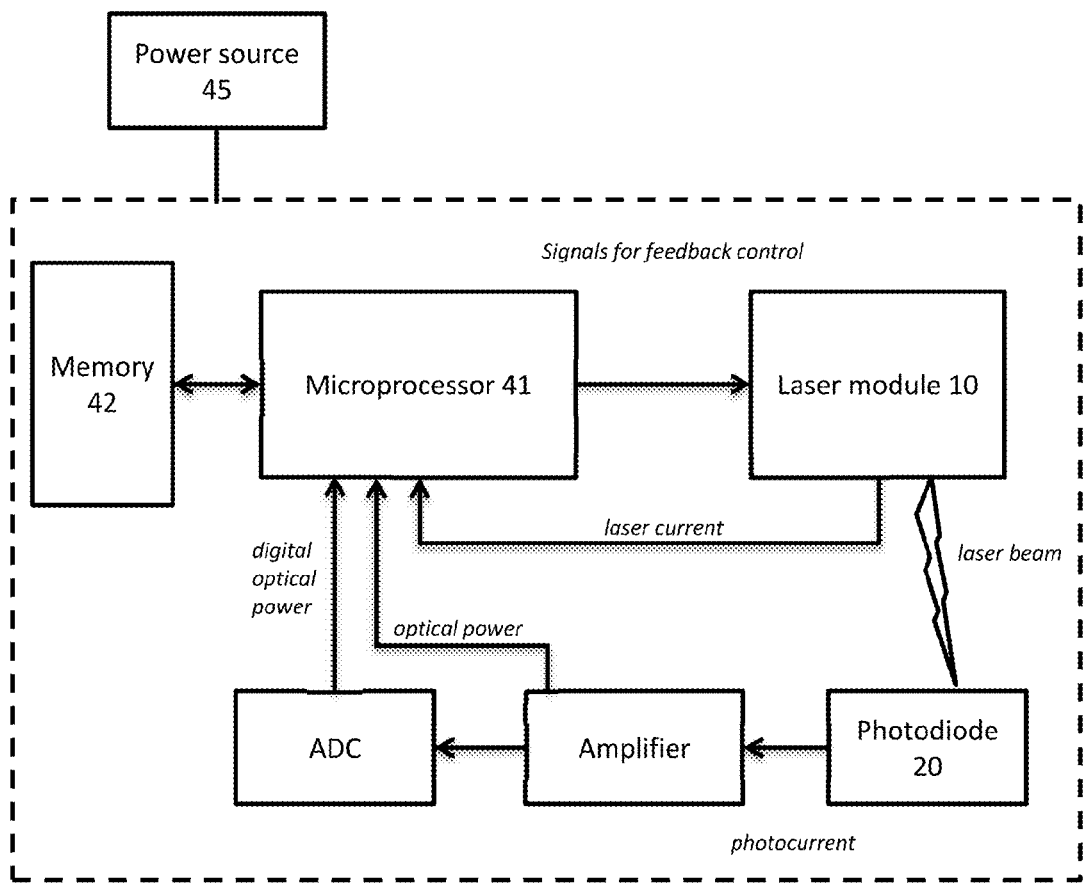
FIG. 3B shows a block diagram depicting an example of feedback control.

In FIG. 3B, an optical measurement device may comprise a light source 10, a collimator 15, a first beam splitter 31, a second beam splitter 32, a first light receiving module 21, a second light receiving module 22, a microprocessor 41, a power source 45, a memory 42, and a zeroth light receiving module 20. For example, the light source may be a laser module 10 when an optical measurement device with feedback control process. The zeroth light receiving module 20 may be a photodiode 20 for detecting the light beam emitted from the light source and directed by the first beam splitter. In one example, the laser module 10 emits a laser light beam and the laser light beam is detected by the photodiode 20 and converted into the photocurrent. The photocurrent is amplified by an amplifier and the analogue signal of optical power is sent to the microprocessor with an analogue input pin. The microprocessor may fetch a preset feedback control function from the memory to determine the feedback control signals according to the analogue signal and control the laser power of the laser module. In one example, the amplified photocurrent may be converted into digital optical power by an ADC and then sent to the microprocessor. The microprocessor may fetch a preset feedback control function from the memory to determine the feedback control signals to control the laser power of the laser module. In addition to the examples, laser module may send a laser current back to the microprocessor as one of the determinant of the feedback control function. In one example, the microprocessor, amplifier, ADC, memory may all be integrated in a single compact chip.

Figure 3C:
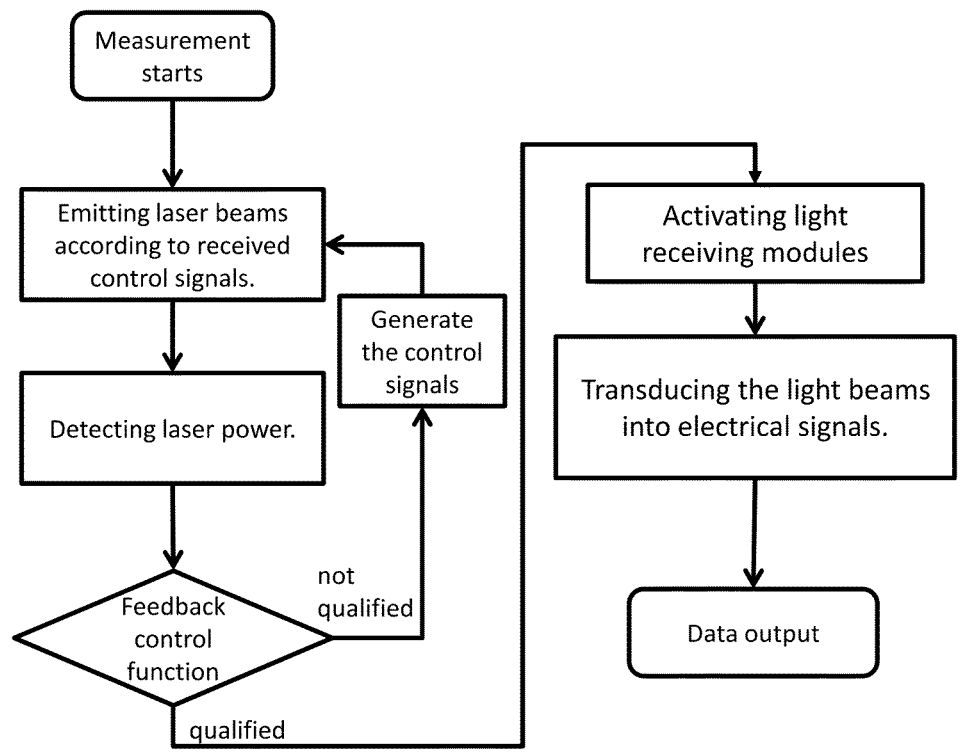
FIG. 3C shows a flow diagram demonstrating the process of feedback control.

In FIG. 3C, the flow diagram shows the feedback control process of the optical measurement device. A laser driver receives the control signals from a microprocessor 41 to trigger a laser diode to emit original light beam. The original light beam 110 is converted to the collimated light beam 115 by the collimator 15 and a part of the collimated light beam 115 is guided by the first beam splitter 31 as a feedback light beam 125, which travels from the first beam splitter 31 to the zeroth light receiving module 20. Then, the feedback light beam 125 is received by the zeroth light receiving module 20, by which the laser power intensity is delivered to the microprocessor 41, and the feedback control function is capable of deciding whether the laser power is qualified to measure the analyte 99. The laser power may be gradually increased by the indication of the control signals, if the laser power is too low for measurement. When a qualified laser power is detected, the zeroth light receiving module is activated to transduce the feedback light beam 125 into electrical signals. It is contemplate that the laser driver and the laser diode may be integrated in a laser module as a light source 10 in the optical measurement device.

An optical measurement module may further comprise a third beam splitter and a third light receiving module. The third beam splitter directs a second part of the measurement light beam to the third light receiving module. The third light receiving module may be a thermometer, a telemeter or an image sensor.

Figure 4:
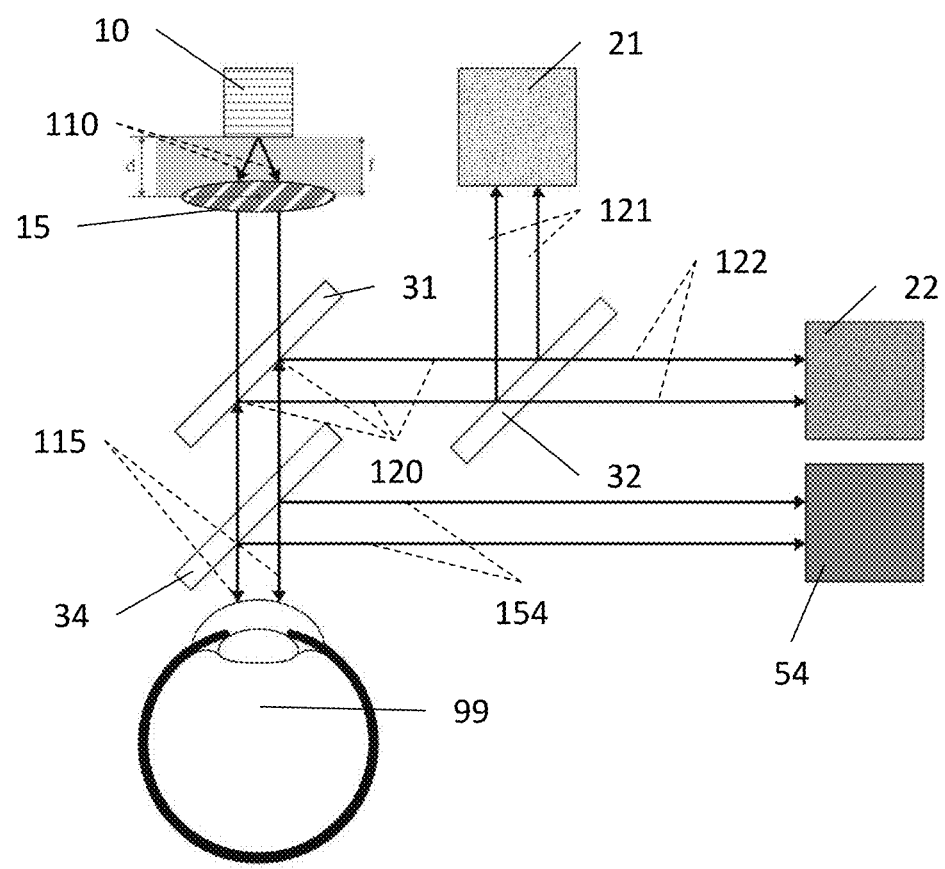
FIG. 4 illustrates an example of the present disclosure with a thermometer module and the associated light path.

In FIG. 4, an optical measurement module may further comprise a thermometer beam splitter 34 and a thermometer module 54. The temperature of an analyte 99 influences the measured optical properties, such as optical rotation. Thus, the temperature is an essential parameter for the calculation of the optical properties. A thermometer module 54 is configured to measuring the temperature of the object of interest. People may appreciate that the optical measurement device comprising the optical measurement module may obtain the temperature right at the same region as the measured region. The thermometer module 54 may comprise a photodetector and an optical component. The photodetector may be a photodiode, two photodiodes, or a photodiode array, which detects a specific wavelength, two different wavelength, or a spectrum of specific region. In each example, the optical component may be a focusing lens, a dichroic beam splitter, or a dispersion element, respectively.

The thermal radiation light beam 154 is the spontaneously emitted light beam from the analyte 99. The thermal radiation light beam 154 is delivered from the analyte 99 via the thermometer beam splitter 34 to the thermometer module 54. Also, an original light beam 110 becomes a collimated light beam 115 after passing through a collimator 15. A collimated light beam 115 may travel from a collimator 15 via the first beam splitter 31 reaching to an analyte 99. A part of measurement light beam is delivered from the analyte 99 via the thermometer beam splitter 34 to the second beam splitter 32 and then divided into a first detection light beam and a second detection light beam by the second beam splitter 32. A first detection light beam traveled from the second beam splitter 32 is detected by a first light receiving module 21, and a second detection light beam traveled from the second beam splitter 32 is detected by a second light receiving module 22.

In one example, an optical measurement device may comprise a light source 10, a collimator 15, a first beam splitter 31, a second beam splitter 32, a first light receiving module 21, a second light receiving module 22, a microprocessor 41, a power source 45, a memory 42, and a thermometer module 54. The thermometer module 54 receives the thermal radiation light beam 154 from an analyte 99 and transduces the thermal radiation light beam 154 into electrical signals. Then, the microprocessor 41 is able to calculate the temperature according to the received thermal radiation, and the microprocessor 41 may correct the measurement values of the first light receiving module 21 and the second light receiving module 22 according to the measured temperature. It is contemplated that the temperature estimation may be achieved by Stefan-Boltzmann law depending on single wavelength, two wavelength, or a spectrum of thermal radiation.

Figure 5A:
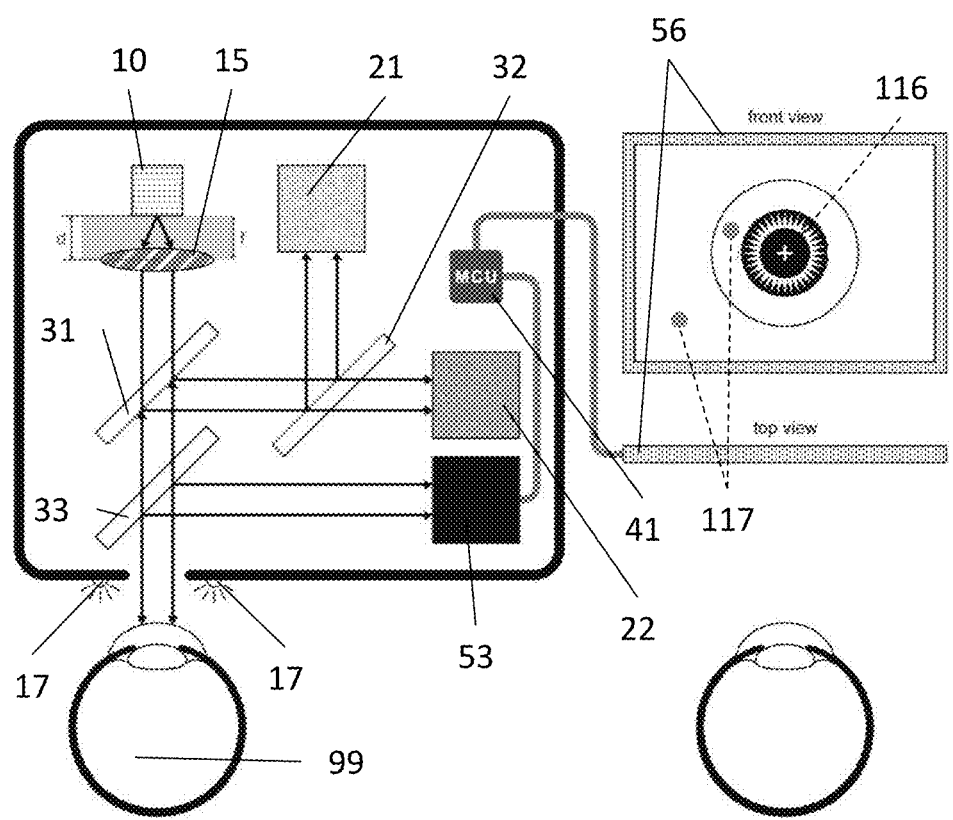
FIG. 5A shows an example of the present disclosure with manual alignment and the associated light path.

In FIG. 5A, an optical measurement device may comprise the optical measurement module, a microprocessor 41, a power source 45, a memory 42, an alignment light emitter 17, an image beam splitter 33, an image sensor 53, and a display 56. An alignment light emitter 17 is configured to generate an alignment light spot 117 from the projection of the alignment light beam on the analyte 99, where the alignment light emitter 17 may be embodied as a LED or a laser diode. An image sensor 53 is configured to capture an image, where the image sensor 53 may comprise an image sensor array, such as charge-coupled device (CCD) or complementary metal-oxide semiconductor (CMOS), and the image may be an instant image or a temporal series of images. An image sensor 53 may further comprise optical components for adequate focusing or imaging. A display 56 is configured to receive and visualize the image information from the microprocessor, where the display 56 may comprise a panel of light emitting elements, such as a liquid crystal display (LCD), light emitting diode (LED), or organic light emitting diode (OLED). An image beam splitter 33 is configured to guide the light beams from the analyte surface to the image sensor 53, while not to alter the optical properties of the measurement light beam. A reference light spot 116 is produced from the projection of the collimated light beam; with factory setup, the reference light spot 116 is always captured in the same region of the image by the image sensor 53 regardless of the relative location of the optical measurement device and the analyte 99. An alignment light spot 117 is produced from the projection of the light beam emitted from an alignment light emitter 17, and is captured by the image sensor 53; an alignment light spot 117 has a variable distance and location relatively from the reference light spot 116. It is contemplated that there may be multiple alignment light emitters 17 producing multiple alignment light spots 117 to have better alignment. People may appreciate that the optical measurement device may be accurately aligned at the same region of an analyte as the measured region.

A method for optical measurement comprises emitting an original light beam to a collimator by a light source, converging the original light beam to a first beam splitter through the collimator, directing a collimated light beam by the first beam splitter to an analyte, redirecting a measurement light beam reflected by the analyte to a second beam splitter, splitting the measurement light beam into a first detection light beam and a second detection light beam, receiving the first detection light beam by the first light receiving module, and receiving the second detection light beam by the second light receiving module. Furthermore, the method for optical measurement may further comprise the steps of the alignment method.

Figure 5B:
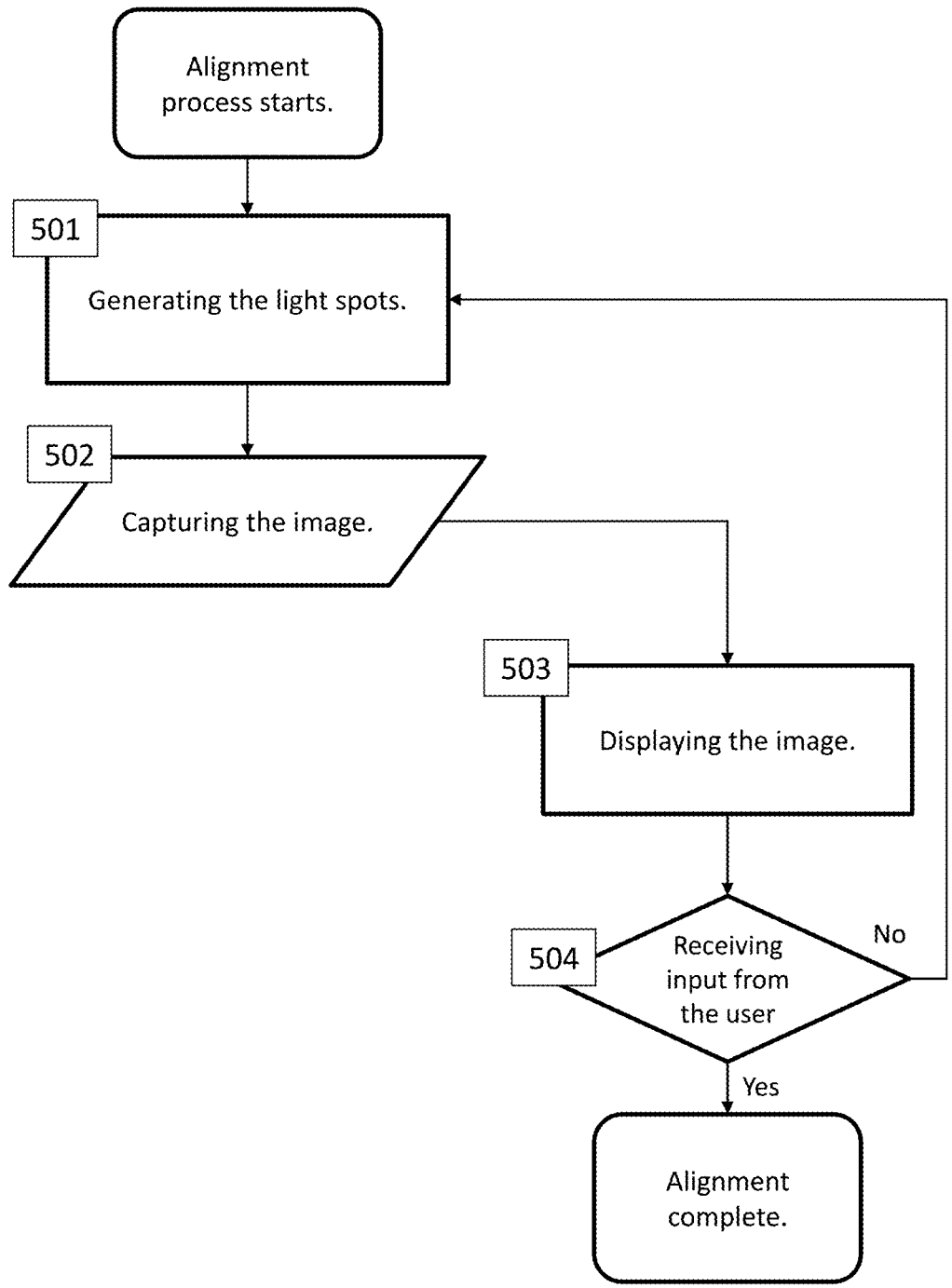
FIG. 5B shows a flow diagram demonstrating the process of manual alignment.

In FIG. 5B, an alignment method may comprise generating the light spots on an analyte surface, wherein the light spots comprise an alignment light spot and a reference light spot; capturing an image comprising the reference light spot, the alignment light spot, and the analyte surface; displaying the image comprising default alignment information, wherein the default alignment information comprises a reference light point, an alignment light point, and a landmark. The alignment method may be performed by an alignment device. The alignment device may comprise a light source that emits a reference light beam; an alignment light emitter that generates an alignment light spot on an analyte; an image beam splitter that directs the reference light beam to form a reference light spot on the analyte; an image sensor that captures an image of the analyte via the image beam splitter; a microprocessor that processes the image for alignment; and a memory that stores the image and a default alignment information, wherein the image comprises characteristics of the reference light spot, the alignment light spot, and the analyte, and wherein the default alignment information comprises a reference light point, an alignment light point, and a landmark. In some examples, the alignment device may further comprise a collimator and the reference light beam is a collimated light beam.

In one example, a user may start a manual alignment process when placing the optical measurement device to the analyte. The default alignment information is stored in the memory 42 including a landmark, a reference point, and an alignment point. In the step 501, the optical measurement device generates the light spots, including a reference light spot and an alignment light spot, on the analyte surface. The collimated light beam projects the reference light spot 116, and an alignment light emitter projects an alignment light spot 117. In the step 502, the image sensor 53 captures the image including the analyte surface, the reference light spot 116 and the alignment light spot 117, and conveys the captured image to the microprocessor 41 in a form of electrical signals. In the step 503, the display 56 displays the captured image comprising the default alignment information delivered from the microprocessor 41. In the step 504, the alignment device may receive a confirmation signal from an user, such as a button press. The default alignment information may be a default setup stored in the memory or may be updated during the alignment method.

Figure 6A:
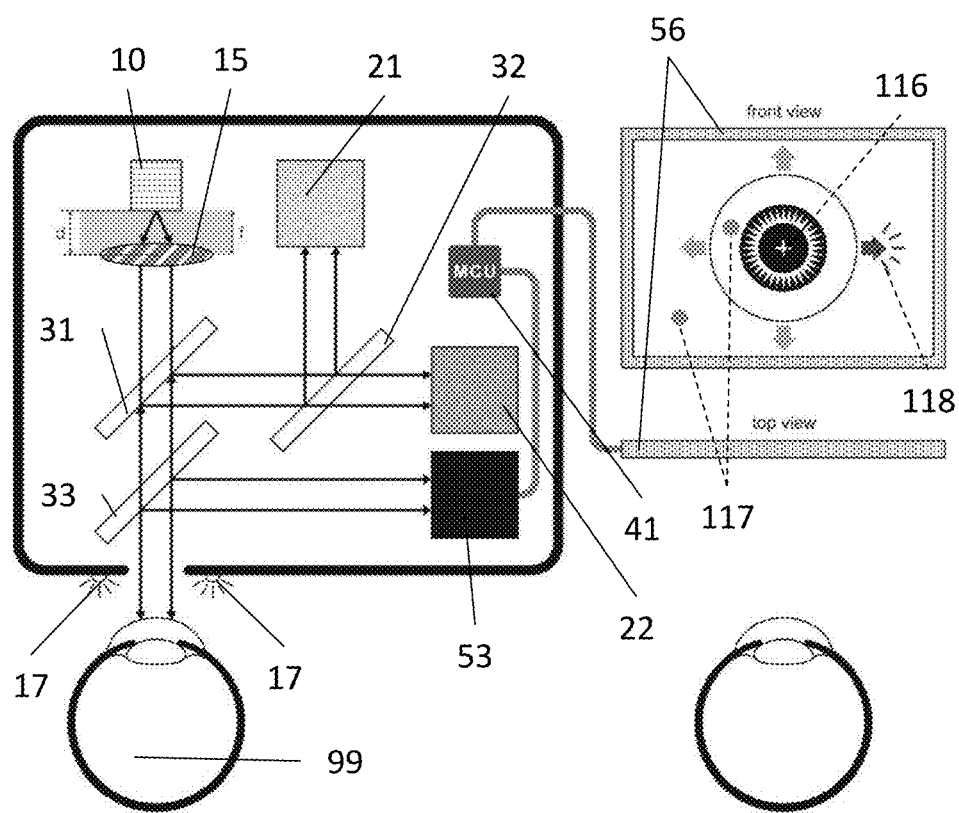
FIG. 6A shows an example of the present disclosure with semi-automatic alignment and the associated light path.

In the example of semi-automatic alignment illustrated in FIG. 6A, an optical measurement device may comprise a light source 10, a collimator 15, a first beam splitter 31, a second beam splitter 32, a first light receiving module 21, a second light receiving module 22, a microprocessor 41, a power source 45, a memory 42, an alignment light emitter 17, an image beam splitter 33, an image sensor 53, and a display 56. The principle of the alignment method is to compare if the acquired alignment information matches the default alignment information. The alignment information includes a landmark, a reference point, and an alignment point. With pattern recognition processed by the microprocessor, the alignment information may be extracted from the captured image; specifically, the landmark may be extracted from the image of the analyte surface, the reference point from the reference light spot 116, the alignment point from the alignment light spot 117. Especially, the landmark may be, for example, the center of the pupil, the outlining of the cornea, or the stripes of the iris. The acquired alignment information is the alignment information acquired during the alignment method. The default alignment information may be a default setup stored in the memory or may be updated during the alignment process.

Figure 6B:
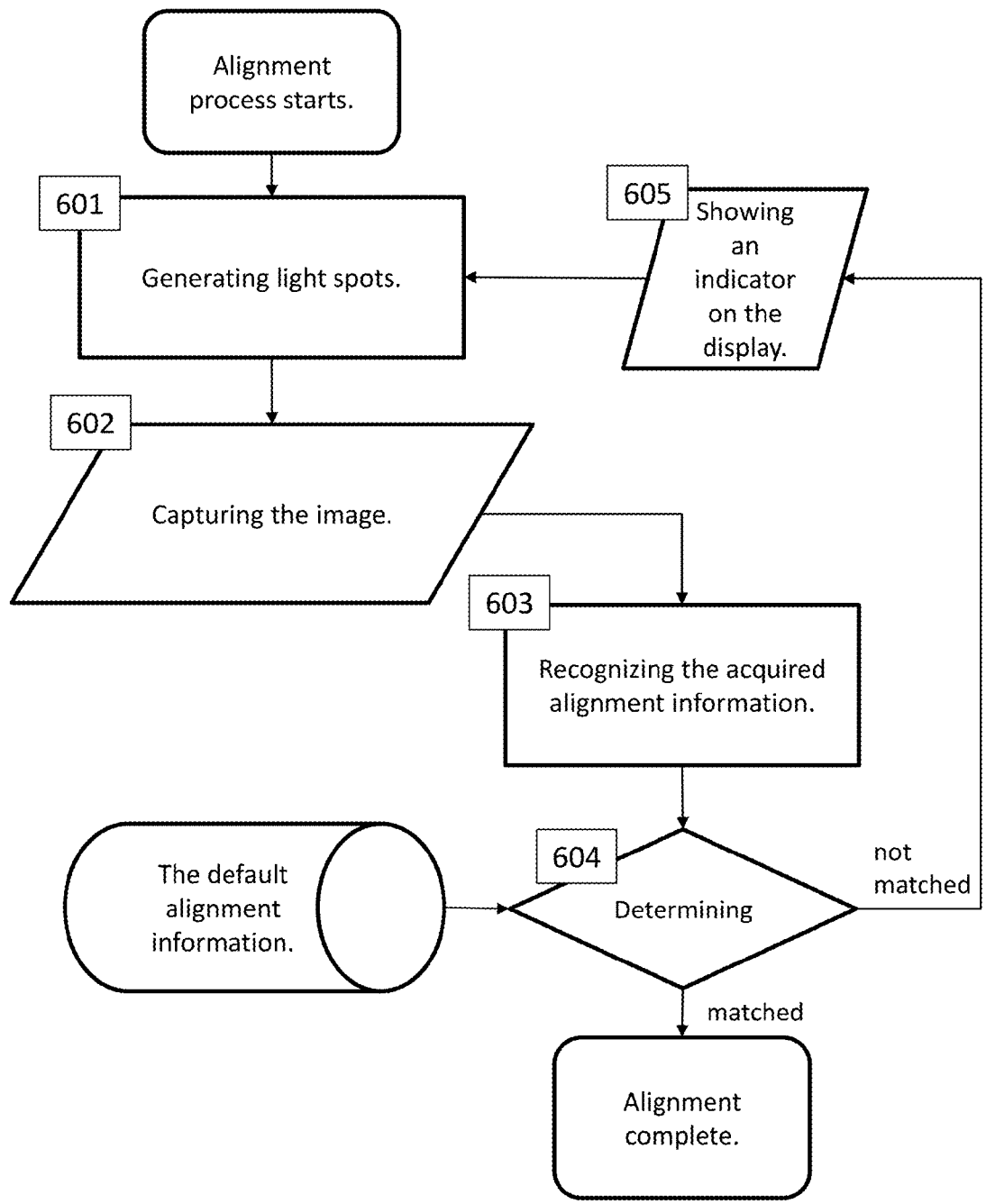
FIG. 6B shows a flow diagram demonstrating the process of semi-automatic alignment.
Figure 6C:
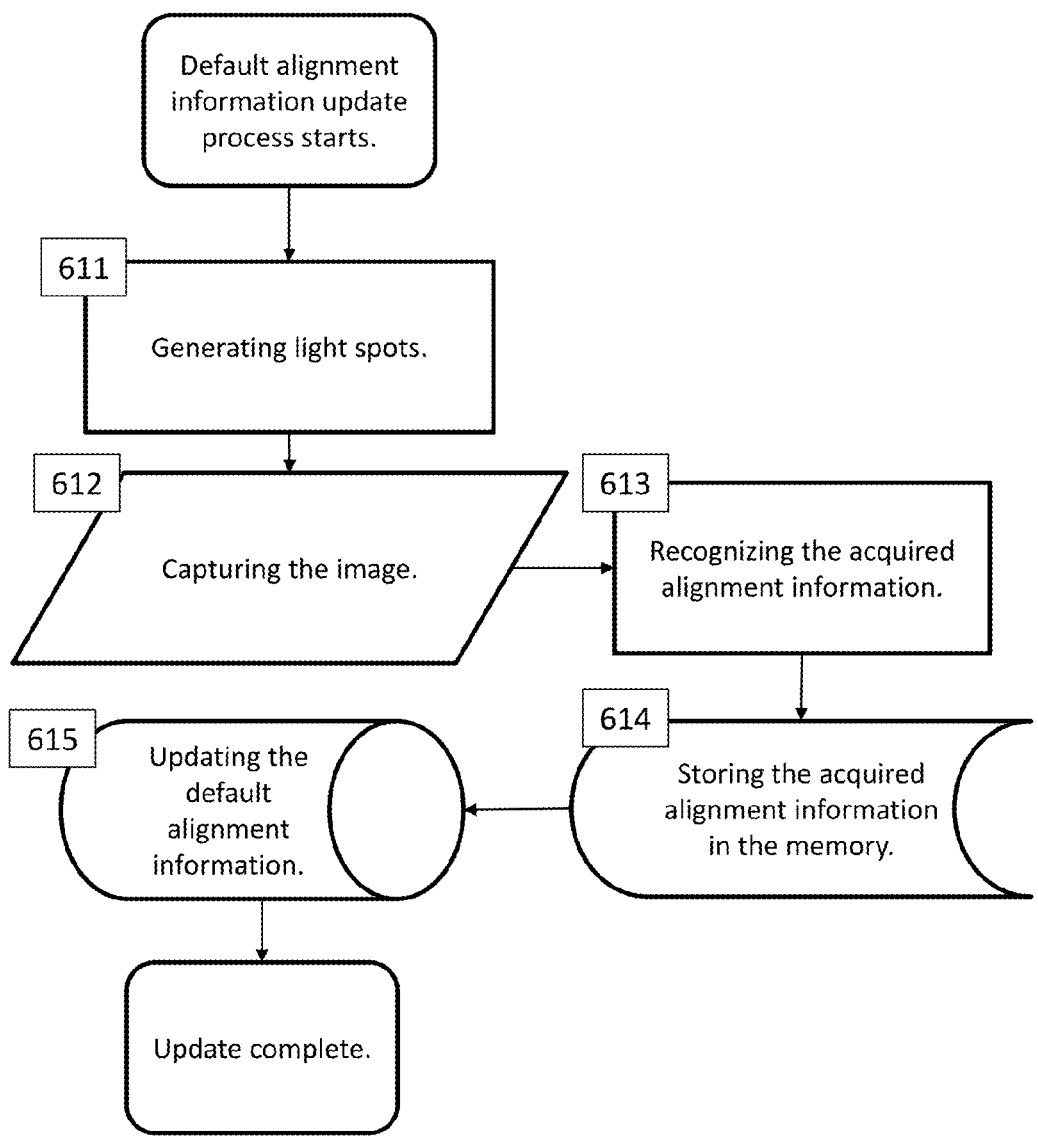
FIG. 6C shows a flow diagram demonstrating the process of updating the default alignment information.

In one example illustrated in FIG. 6B, a user may start a semi-automatic alignment process. First, the user aligns the device to the analyte. In the step 601, the collimated light beam projects reference light spot 116, and an alignment light emitter projects an alignment light spot 117. In the step 602, the image sensor 53 captures the image including the analyte surface, the reference light spot 116 and the alignment light spot 117, and conveys the captured image to the microprocessor 41 in a form of electrical signals. In the step 603, the microprocessor 41 recognizes the acquired alignment information according to the captured image. Then, the display 56 shows the captured image concurrent with the default alignment information delivered from the microprocessor 41. In the step 604, the microprocessor determines the difference between the acquired alignment information and the default alignment information and determines whether the acquired alignment information and the default alignment information are matched. Otherwise 605, the microprocessor shows an indicator 118 on the screen to alert the user that the alignment process needs to be repeated. It is contemplated that the microprocessor is able to calculate the direction of correct alignment and send out an indicator 118 to facilitate the alignment process. In the step 611, the collimated light beam projects reference light spot 116, and an alignment light emitter projects an alignment light spot 117. In the step 612, the image sensor 53 captures the image including the analyte surface, the reference light spot 116 and the alignment light spot 117, and conveys the captured image to the microprocessor 41 in a form of electrical signals. In the step 613, the microprocessor 41 recognizes the acquired alignment information according to the captured image. Then, the display 56 shows the captured image concurrent with the default alignment information delivered from the microprocessor 41. In addition, the default alignment information may be stored 614 and updated 615 from the acquired alignment information during the alignment process depending on the user's request or the success of the alignment process (FIG. 6C).

Figure 7A:
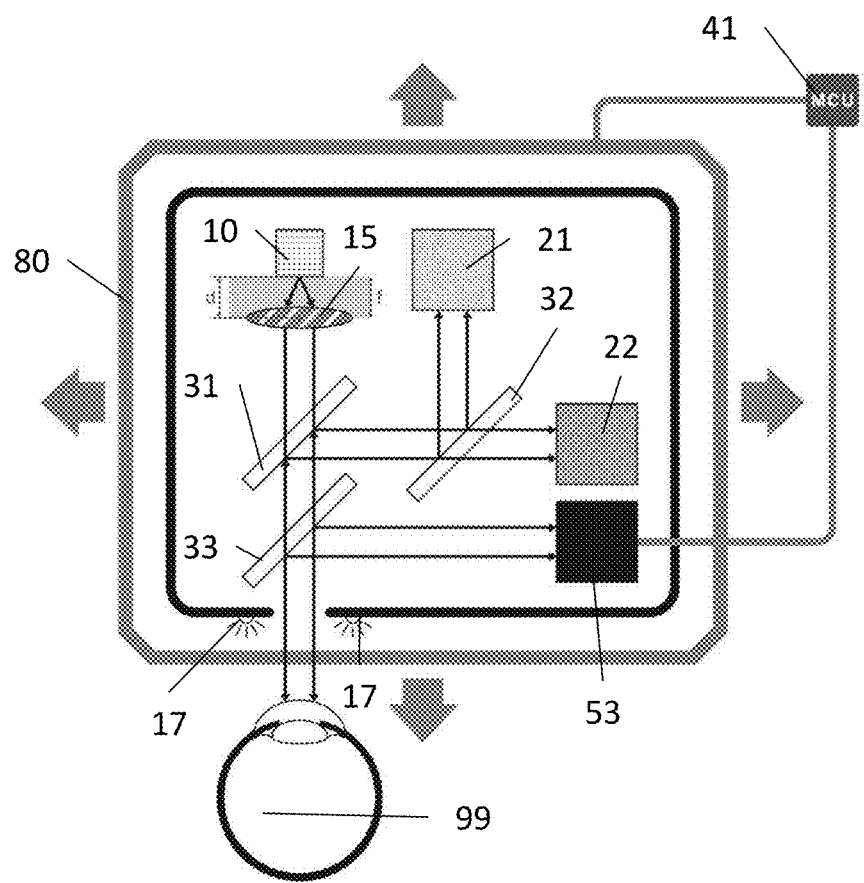
FIG. 7A shows an example of the present disclosure with automatic alignment and the associated light path.

In the example of automatic alignment as illustrated in FIG. 7A, an optical measurement device may comprise a light source 10, a collimator 15, a first beam splitter 31, a second beam splitter 32, a first light receiving module 21, a second light receiving module 22, a microprocessor 41, a power source 45, a memory 42, an alignment light emitter 17, an image beam splitter 33, an image sensor 53, and an actuator module 80.

Figure 7B:
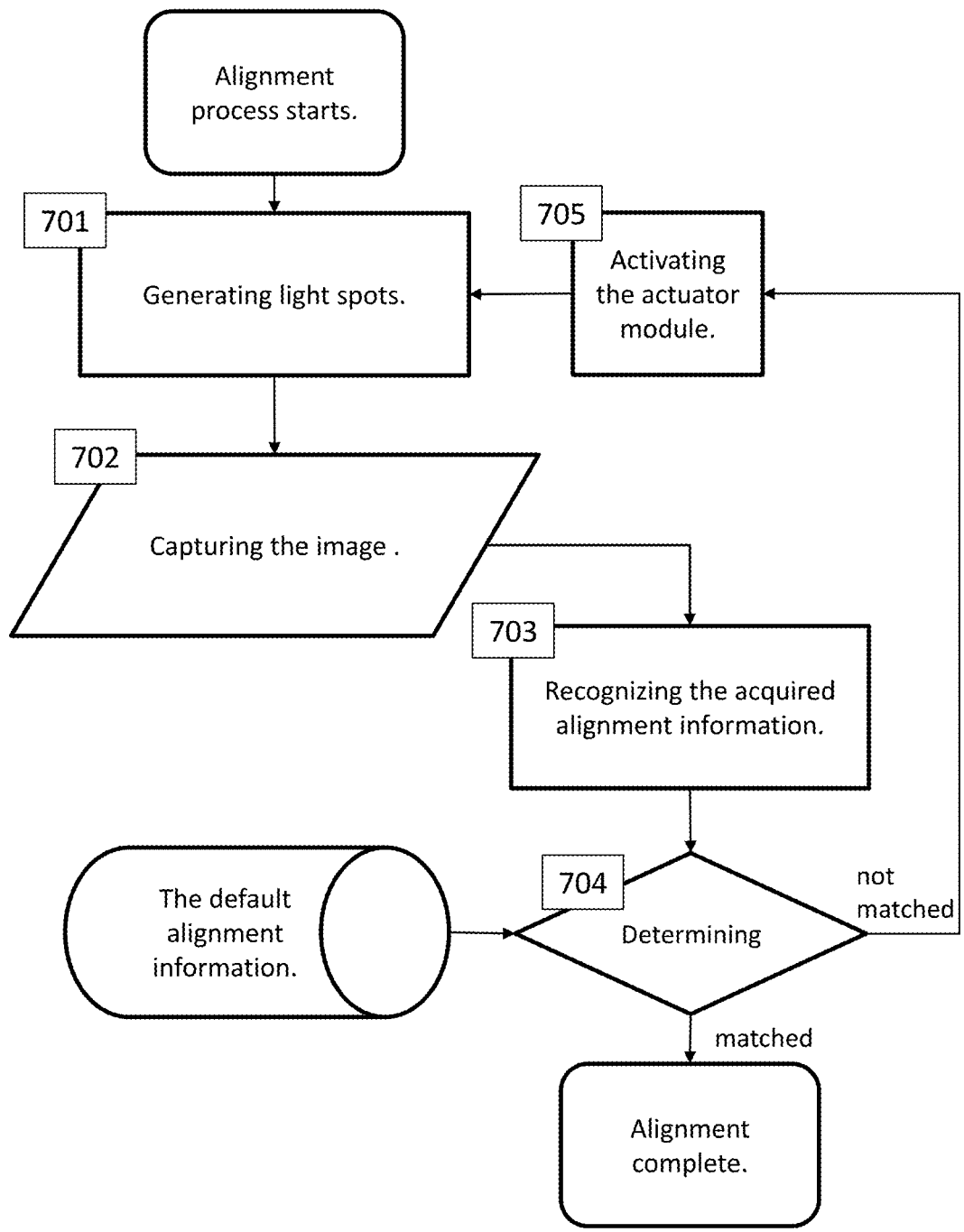
FIG. 7B shows a flow diagram demonstrating the process of measurement and automatic alignment.

In one example as illustrated in FIG. 7B, a user may start an automatic alignment process. First, the user applies the device to the analyte. In the step 701, the collimated light beam projects reference light spot 116, and an alignment light emitter projects an alignment light spot 117. In the step 702, the image sensor 53 captures the image including the analyte surface, the reference light spot 116 and the alignment light spot 117, and conveys the captured image to the microprocessor 41 in a form of electrical signals. In the step 703, the microprocessor recognizes the acquired alignment information according to the captured image. In the step 704, the microprocessor determines the difference between the acquired alignment information and the default alignment information and determines whether the acquired alignment information and the default alignment information are matched. Otherwise 705, the microprocessor is able to calculate the direction of correct alignment and activates the actuator module 80 to repeat the alignment process. In addition, the default alignment information may be stored 614 and updated 615 from the acquired alignment information during the alignment process depending on the user's request or the success of the alignment process (FIG. 6C).

Figure 7C:
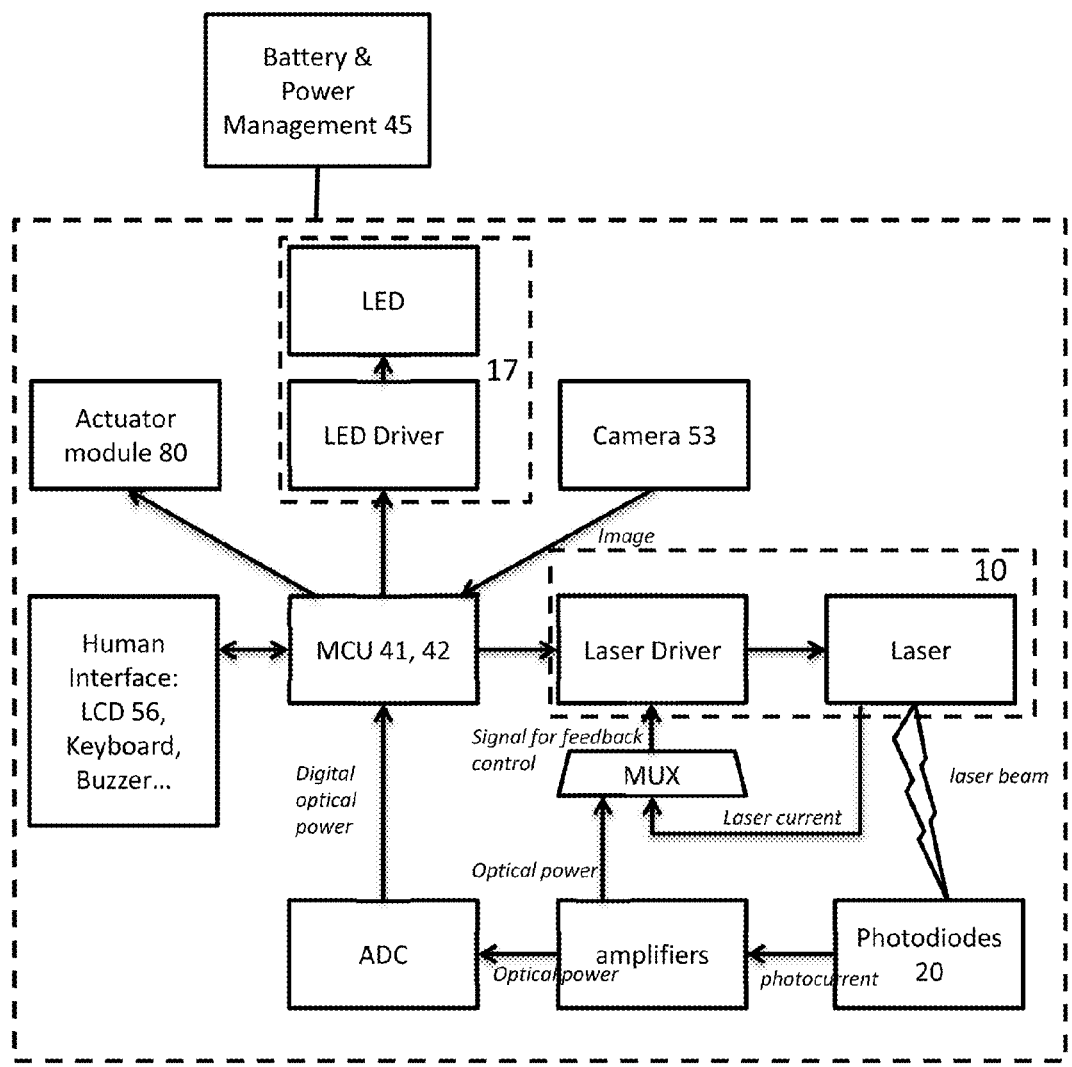
FIG. 7C shows an example of the present disclosure with automatic alignment and feedback control.

An optical measurement device with both alignment and feedback control. The optical measurement device may comprise a light source 10, a collimator 15, a first beam splitter 31, a second beam splitter 32, a zeroth light receiving module 20, a first light receiving module 21, a second light receiving module 22, a microprocessor 41, a power source 45, a memory 42, an alignment light emitter 17, an image beam splitter 33, an image sensor 53, a display 56 and an actuator module 80. As shown in FIG. 7C, the components mentioned above may be embodied with commercialized products, such as a MCU as a microprocessor 41r with memories 42, a laser with laser driver as a light source, LED with LED driver as an alignment light emitter 17. It is contemplated that the optical measurement device may further comprise human interfaces (e.g., LCD, keyboard, touch panel, or speakers), a multiplexer (MCX), amplifiers and ADCs for a user friendly environment and delicate signal processing.

An optical measurement device may comprise a light source 10, a collimator 15, a first beam splitter 31, a second beam splitter 32, a first light receiving module 21, a second light receiving module 22, a microprocessor 41, a power source 45, a memory 42, and a spatial sensor. A spatial sensor is configured to detect the relative spatial position, movement, and inclination of the device and to assist better alignment of the measurement device for measurement accuracy and consistency. The spatial sensor may be an inertial sensor 52 to detect the acceleration or the inclination, a telemeter 55 to detect the distance between the optical measurement device and the analyte, or the combination to gather further spatial information. Here, the inertial sensor 52 may be an accelerometer or a gyroscope.

Figure 8:
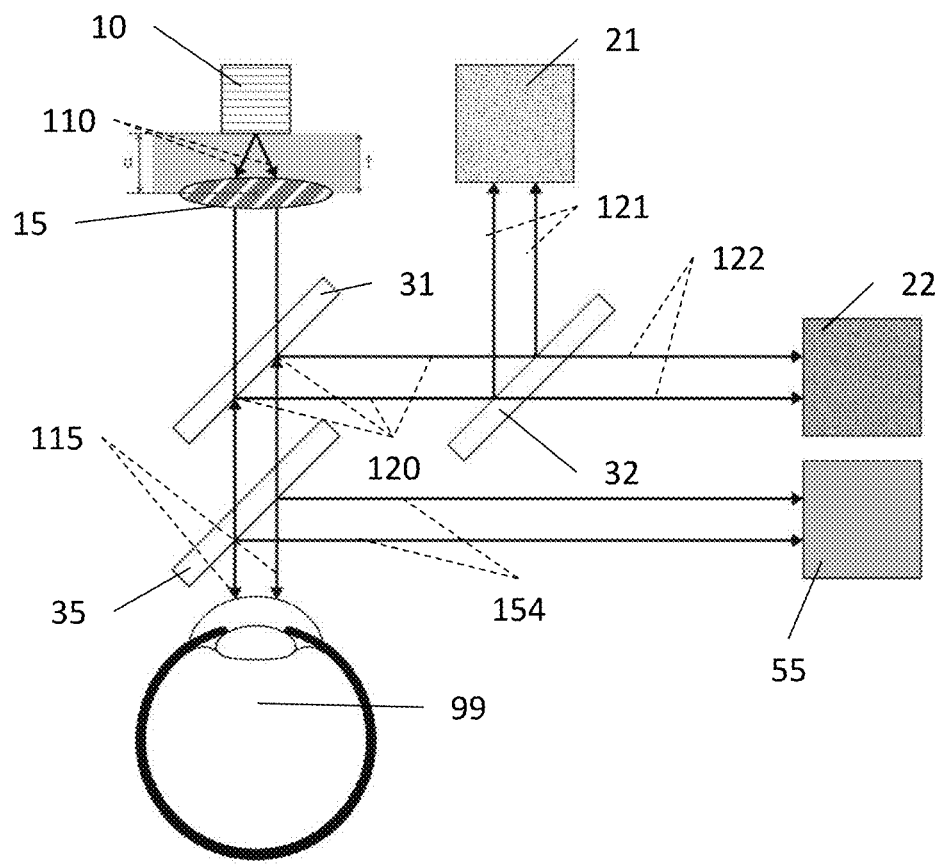
FIG. 8 illustrates an example of the present disclosure with a telemeter and the associated light path.

Practically, the power intensity of light beams may dissipate along the traveling distance. In some examples, the measurement distance influences not only the alignment consistency but also the baseline reference of detected power intensity. Therefore, a baseline of power intensity correction is necessary for accurate measurement. People may appreciate that the optical measurement device may obtain the distance from the same region of an analyte as the measured region. As illustrated in FIG. 8, an optical measurement device may comprise a light source 10, a collimator 15, a first beam splitter 31, a second beam splitter 32, a first light receiving module 21, a second light receiving module 22, a microprocessor 41, a power source 45, a memory 42, and a telemeter 55, which is configured to detect the distance between the analyte 99 and the device and to assist better alignment of the measurement device for measurement consistency. Here, the telemeter 55 may be a fast-response photodetector coupled to the microprocessor 41 to calculate the distance by time of flight between the light source 10 and the telemeter 55 or may be an interferometer to obtain the distance by interference.

In the example, an original light beam 110 becomes a collimated light beam 115 after passing through a collimator 15. A collimated light beam 115 may travels from a collimator 15 via the first beam splitter 31 reaching to an analyte 99. A first part of measurement light beam is delivered from the analyte 99 via the telemeter beam splitter 35 to the telemeter 55; a second part of measurement light beam is delivered from the analyte 99 via the telemeter beam splitter 35 to the second beam splitter 32 and then divided into a first detection light beam and a second detection light beam by the second beam splitter 32. A first detection light beam traveled from the second beam splitter 32 is detected by a first light receiving module 21, and a second detection light beam traveled from the second beam splitter 32 is detected by a second light receiving module 22.

An optical measurement device may comprise a light source 10, a collimator 15, a first beam splitter 31, a second beam splitter 32, a first light receiving module 21, a second light receiving module 22, a microprocessor 41, a power source 45, a memory 42, and an inertial sensor 52. An inertial sensor 52 is configured to detect the relative spatial position, movement, and inclination of the device and to assist better alignment of the measurement device for measurement consistency. Here, the inertial sensor 52 may be an accelerometer or a gyroscope to detect the acceleration or the inclination of the optical measurement device.

Both telemeter 55 and inertial sensor 52 may provide extra spatial information to assist the alignment of the optical measurement device. In the example of manual alignment, the spatial information may be shown on the display 56 and indicate the user to achieve desired alignment. In the example of semi-automatic alignment, the optical measurement device may calculate the relative location between the optical measurement device and the analyte 99 according to the spatial information and the alignment information, so that it may show an indicator 118 assisting the user to correctly align the optical measurement device. Furthermore, the automatic alignment may be accomplished by controlling the actuator module 80 according to the spatial information and the alignment information.

Figure 9A:
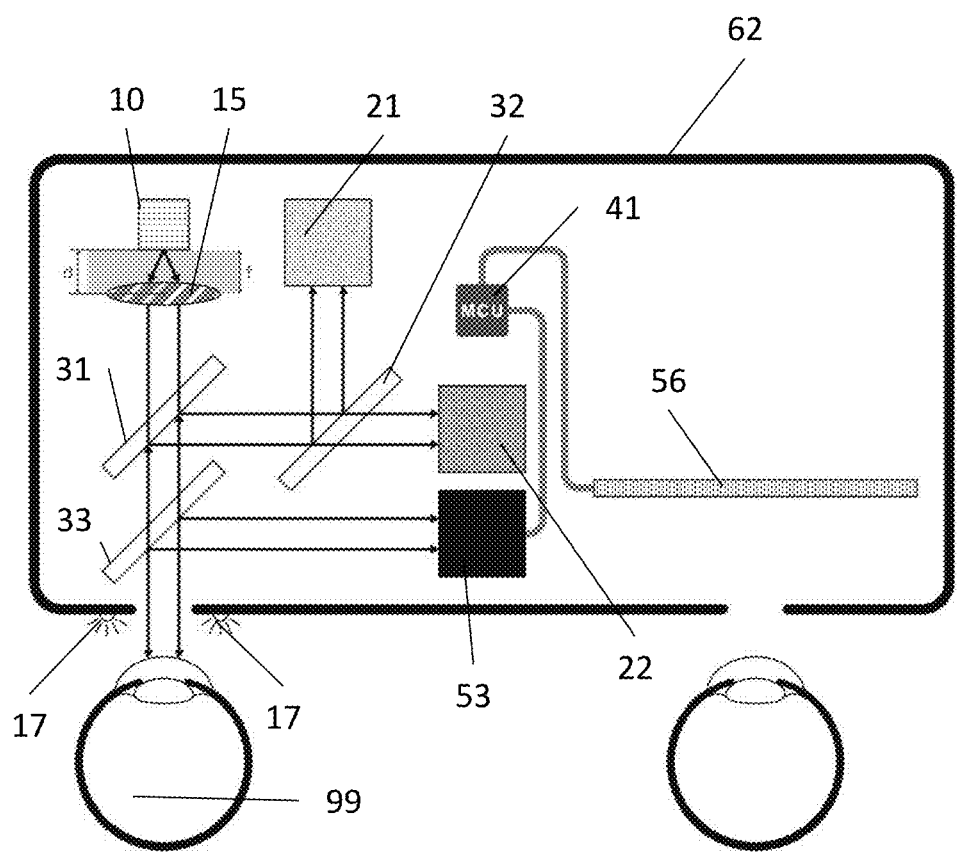
FIG. 9A is an example of an optical measurement device comprising a binocular housing.
Figure 9B:
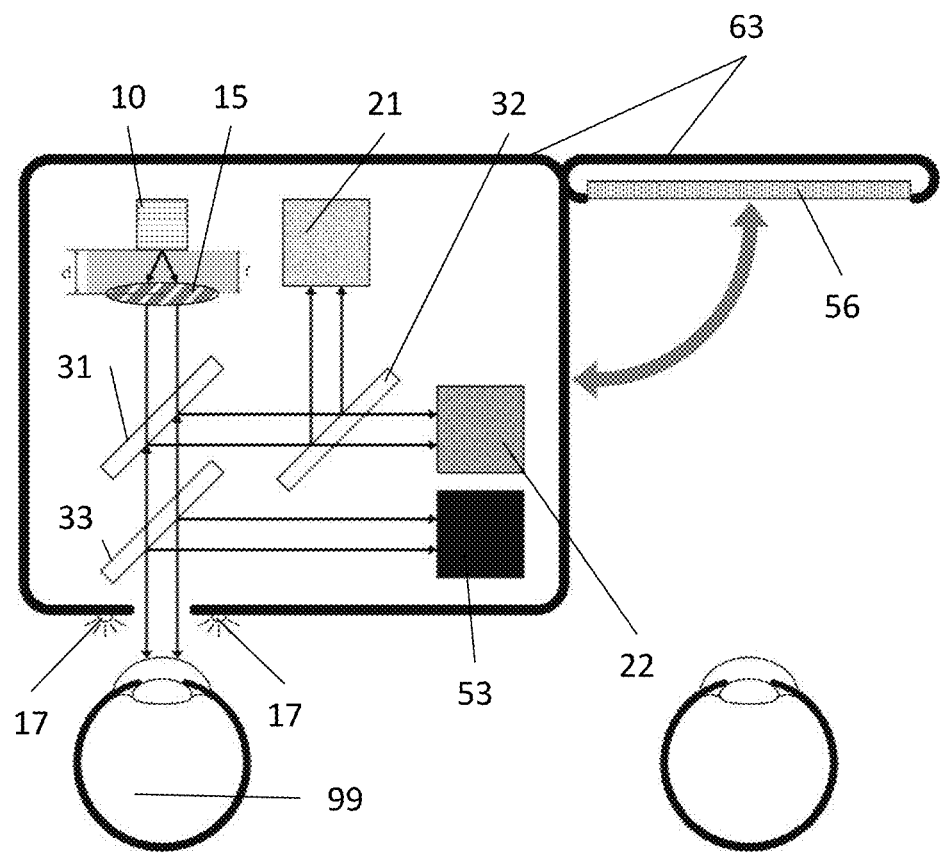
FIG. 9B is an example of an optical measurement device comprising a foldable housing.
Figure 9C:
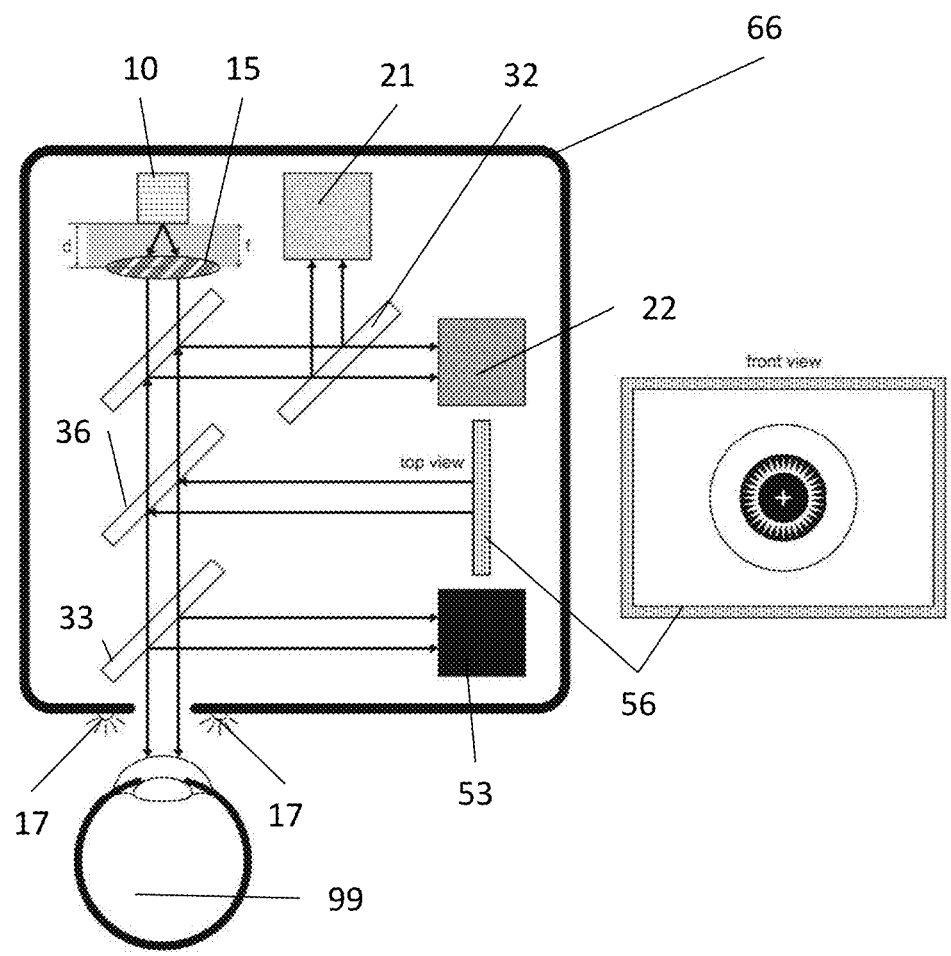
FIG. 9C is an example of an optical measurement device comprising a monocular housing.

As illustrated in FIG. 9A-C, an optical measurement device may comprise a light source 10, a collimator 15, a first beam splitter 31, a second beam splitter 32, a first light receiving module 21, a second light receiving module 22, a microprocessor 41, a power source 45, a memory 42, an alignment light emitter 17, an image beam splitter 33, an image sensor 53, a display 56, and a handheld housing. The optical measurement device may be applied to the ophthalmology to measure the analyte 99 in the eyeball, such as glucose, lactic acid, hemoglobin, oxyhemoglobin, urea, alcohol, or cancer cell. However, the accuracy and consistency of ophthalmological measurement should be based on a good alignment and practical handling. Specifically, the handheld housing is configured to facilitate the alignment process and to integrate all the components.

In the example of the binocular optical measurement device, the optical measurement device further comprises a binocular handheld housing 62 (FIG. 9A). A binocular handheld housing 62 is configured to accommodate all the components of the optical measurement device. The binocular handheld housing 62 comprises a measurement window and an observation window. The measurement window is configured to allow the light path for the collimated light beam 115 and the measurement light beam. As well, the image sensor 53 may capture the image of the eye of interest and the alignment light spots 117 via the image beam splitter 33. The observation window is configured to allow the opposite eye to observe the display 56 showing the image information processed by the microprocessor 41.

In the example of the foldable optical measurement device, the optical measurement device further comprises a foldable handheld housing 63 (FIG. 9B). A foldable handheld housing 63, comprises a foldable frame and an ocular barrel. The foldable frame is configured to accommodate the display 56, and the ocular barrel is configured to accommodate the rest components of the optical measurement device. The ocular barrel comprises a measurement window configured to allow the light path for the collimated light beam 115 and the measurement light beam. As well, the image sensor 53 may capture the image of the eye of interest and the alignment light spots 117 via the image beam splitter 33. The foldable frame is configured to accommodate the display 56 and allow the opposite eye to observe the display 56 showing the image information processed by the microprocessor 41.

In the example of the monocular optical measurement device, the optical measurement device further comprises a monocular handheld housing and a display beam splitter 36 (FIG. 9C). A monocular handheld housing 66 is configured to accommodate all other components of the alignment device and facilitate self-measurement and alignment with single eye. The monocular handheld housing 66 also comprises a measurement window configured to allow the light path for the collimated light beam 115 and the measurement light beam. As well, the image sensor 53 may capture the image of the eye of interest and the alignment light spots 117 via the image beam splitter 33. The same eye of interest may observe the display 56 showing the image information projected on the display beam splitter 36.

Figure 10A:
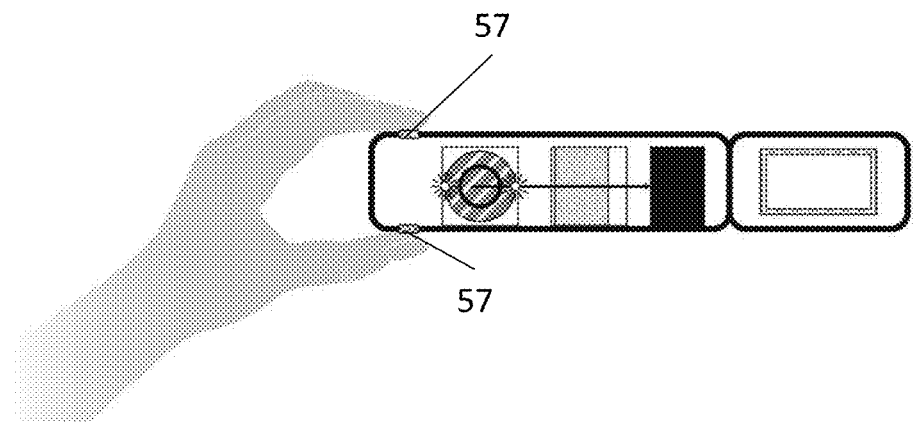
FIG. 10A is an example of an optical measurement device from the view of an user using one-hand grip.
Figure 10B:
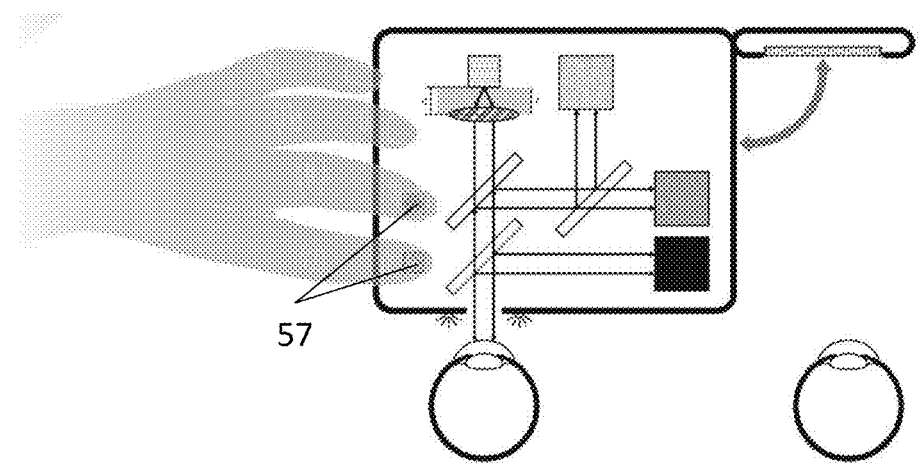
FIG. 10B is a top view of an optical measurement device and an user using one-hand grip.
Figure 10C:
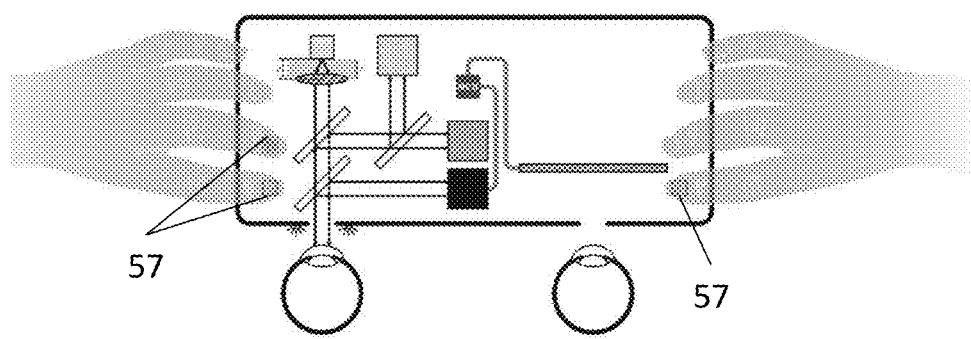
FIG. 10C a top view of an optical measurement device and an user using two-hand grip.

As shown in FIG. 10A-C, an optical measurement device may comprise the optical measurement module and a sensor module 57. A sensor module 57 is configured to provide extra physiological information at the time when the user is using the optical measurement device. The sensor module 57 may be embodied as a reflective pulse oximeter to measure the saturation of blood oxygen, an electrode to measure the electrical impedance of the skin, or a dual sensor module to measure multiple physiologic parameters through a simple touch. Also, multiple sensor modules 57 may be mounted on the opposite side of the handheld housing (FIG. 10A). With one hand grip, multiple physiologic parameters may be measured on each independent sensor module 57 (FIG. 10B). In the example of two hand grip, the sensor modules 57 are capable of acquiring an electrocardiography (ECG) by measuring the electrical potential difference of the two hands (FIG. 10C). Furthermore, blood pressure may be estimated by the pulse transit time derived from blood oxygen saturation and ECG.

At the age of present disclosure, the modules of the electronics, optoelectronics, optomechanics, and optics may be realized in compact size, so that the integration of said optical measurement device may be embodied as a mobile device (e.g., an optical measurement watch) or an accessory of the smart devices (e.g., smart watches, smart phones, tablets, ultrabooks). The optical measurement device may be integrated as a part of the smart device and share the computing resources (e.g., MCU, storage media, communication modules), and the human interfaces (e.g., handheld housing, touch screen panel, virtual reality goggle, HUD helmet). It is contemplated that the optical measurement device may also be an appcessory, an accessory device connecting to a smart device via an app. Furthermore, the measurement data may be transmitted to a cloud server for big data or statistics applications.

Figure 11A:
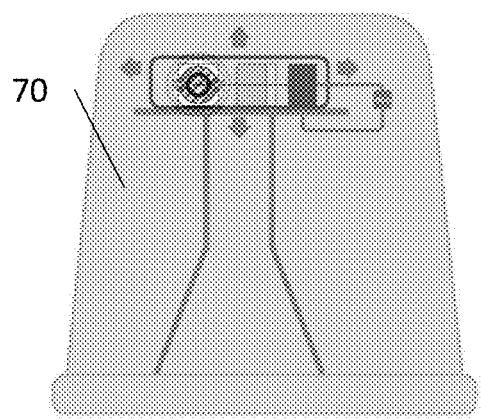
FIG. 11A is a side view of an example of an optical measurement device comprising a platform housing.
Figure 11B:
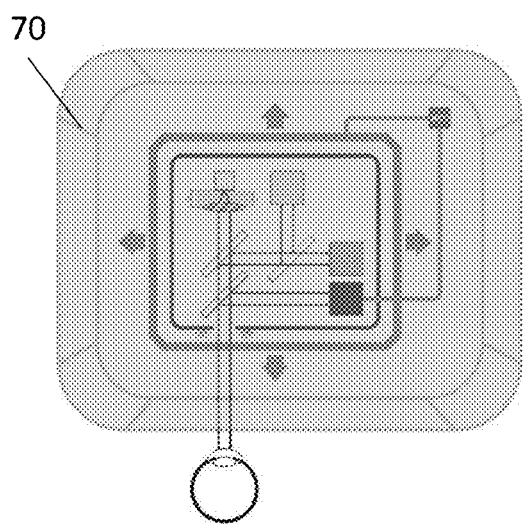
FIG. 11B is a top view of an optical measurement device comprising a platform housing.

As shown in FIG. 11A and FIG. 11B, an optical measurement device may comprise the optical measurement device and a platform housing 70. The platform housing 70 may comprise a connector module, a stand, and a housing. The connector module may provide mechanical connection and/or electrical connection between the optical measurement device and the platform housing 70. With mechanical connection, the optical measurement device is steadily fixed on the connector module, so that the spatial position and inclination can be initialized to the original status. Also, the connector module may provide electrical power and electrical signals to the optical measurement device through electrical connection. Moreover, the platform housing 70 may further comprise an actuator module 80 configured to assist alignment. In the examples, the user may control the actuator module 80 to align the optical measurement device or may control the actuator module 80 according to the indicator 118 showing on the display 56. In addition, the actuator module 80 may adjust the alignment according to the electrical signals sent out by the microprocessor 41 to achieve automatic alignment.

In ophthalmologic measurement techniques, alignment is essential for measurement accuracy and consistency. Current technology allows an operator to achieve acceptable alignment of a measurement device and a patient's eye. With the growing need of personal health care, however, self-alignment without external assistance still remains unmet. The present disclosure provides a solution to self-alignment and it may be reasonably integrated into other ophthalmologic measurement device to aid personal health care and mobile use.

An alignment device may comprise a light source that emits a reference light beam; an alignment light emitter that generates an alignment light spot on an analyte; an image beam splitter that directs the reference light beam to form a reference light spot on the analyte; an image sensor that captures an image of the analyte via the image beam splitter; a microprocessor that processes the image for alignment; and a memory that stores the image and a default alignment information, wherein the image comprises characteristics of the reference light spot, the alignment light spot, and the analyte, and wherein the default alignment information comprises a reference light point, an alignment light point, and a landmark. Furthermore, the alignment device may spare a light path for a first light receiving module. In the examples, the first light receiving module may be applied to the alignment device to acquire specific optical information depending on its measurement purpose. People may appreciate that the optical measurement device may be accurately aligned at the same region of an analyte as the measured region.

Figure 12A:
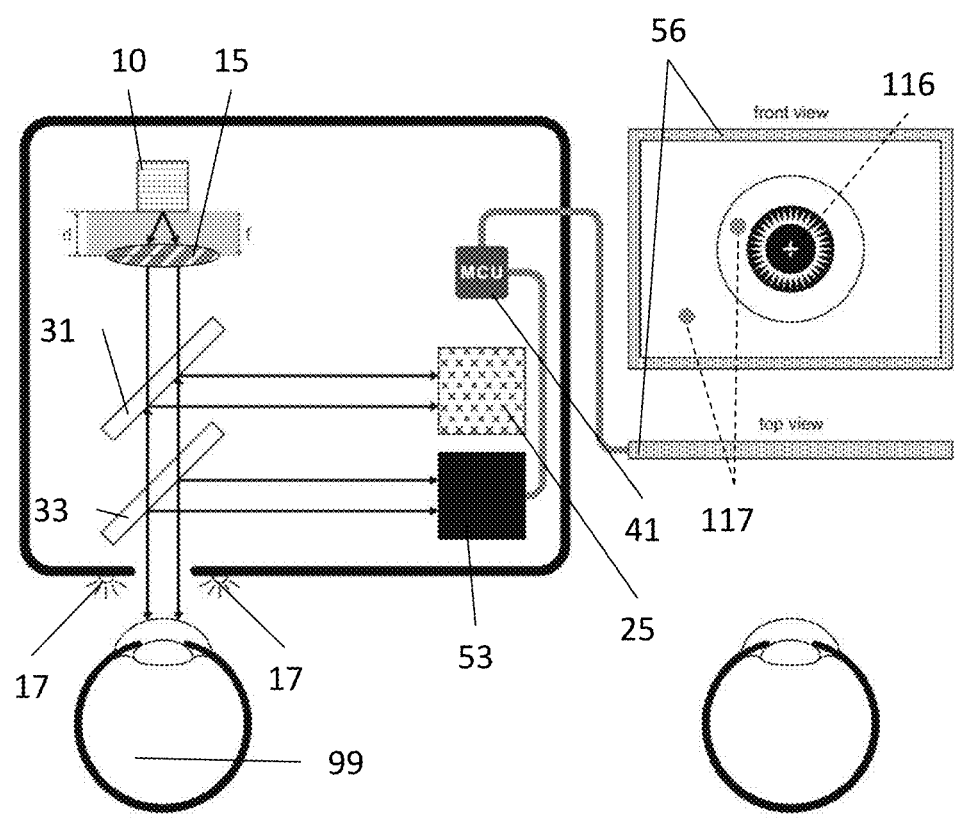
FIG. 12A shows an example of the present disclosure with manual alignment and the associated light path.

In FIG. 12A, an alignment device may comprise a light source 10, a collimator 15, a first beam splitter 31, a microprocessor 41, a power source 45, a memory 42, an alignment light emitter 17, an image beam splitter 33, an image sensor 53, and a display 56. An alignment light emitter 17 is configured to generate an alignment light spot 117 from the projection of the alignment light beam on the analyte 99, where the alignment light emitter 17 may be embodied as a LED or a laser diode. An image sensor 53 is configured to capture an image, where the image sensor 53 may comprise an image sensor array, such as charge-coupled device (CCD) or complementary metal-oxide semiconductor (CMOS), and the image may be an instant image or a temporal series of images. A display 56 is configured to receive and visualize the captured images and the image information from the microprocessor, where the display 56 may comprise a panel of light emitting elements, such as liquid crystal display (LCD), light emitting diode (LED), or organic light emitting diode (OLED). An image beam splitter 33 is configured to guide the light beams from the analyte surface to the image sensor 53, while not to alter the optical properties of the measurement light beam. A reference light spot 116 is produced from the projection of the collimated light beam; with factory setup, the reference light spot 116 is always captured in the same region of the image by the image sensor 53 regardless of the relative location of the alignment device and the analyte 99. An alignment light spot 117 is produced from the projection of the light beam emitted from an alignment light emitter 17, and is captured by the image sensor 53; an alignment light spot 117 has a variable distance and location relatively from the reference light spot 116. It is contemplated that there may be multiple alignment light emitters 17 producing multiple alignment light spot 117 to have better alignment.

Figure 12B:
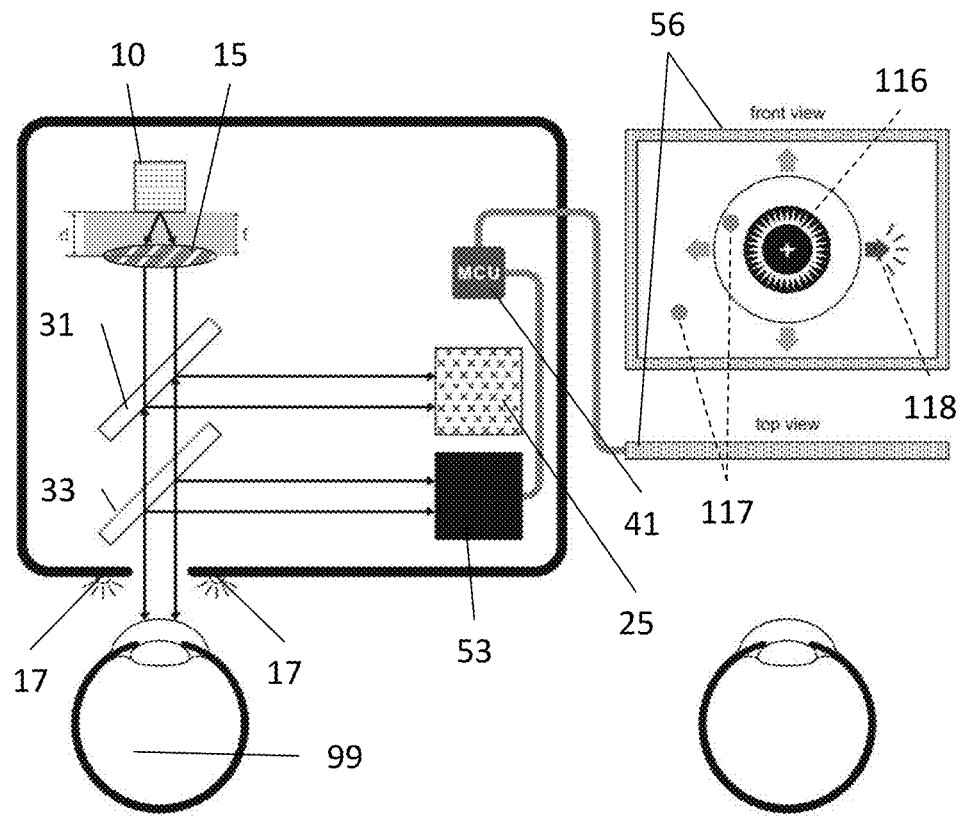
FIG. 12B shows an example of the present disclosure with semi-automatic alignment and the associated light path.

In FIG. 12B, an alignment device may comprise a light source 10, a collimator 15, a first beam splitter 31, a microprocessor 41, a power source 45, a memory 42, an alignment light emitter 17, an image beam splitter 33, an image sensor 53, and a display 56. The alignment method is to determine whether the acquired alignment information matches the default alignment information. The alignment information includes a landmark, a reference point, and an alignment point. With pattern recognition processed by the microprocessor, the alignment information may be extracted from the captured image; specifically, the landmark may be extracted from the image of the analyte surface, the reference point from the reference light spot 116, the alignment point from the alignment light spot 117. Especially, the landmark may be, for example, the center of the pupil, the outlining of the cornea, or the stripes of the iris. The acquired alignment information is the alignment information acquired during the alignment process. The default alignment information may be a default setup stored in the memory or may be updated during the alignment process.

Figure 12C:
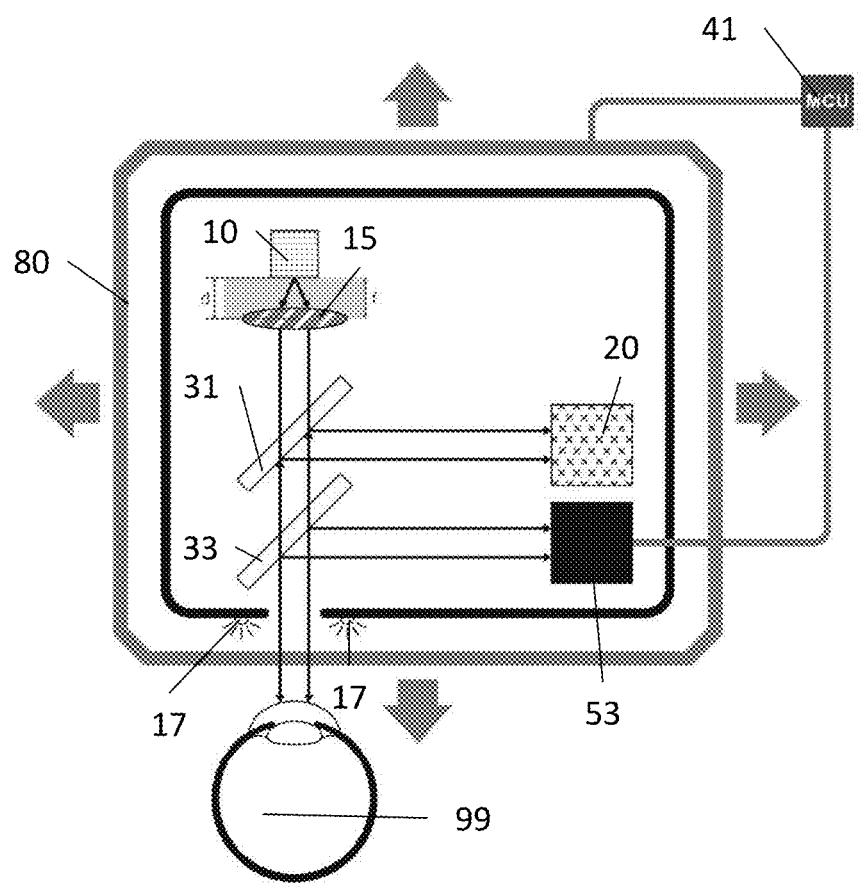
FIG. 12C shows an example of the present disclosure with automatic alignment and the associated light path.

In FIG. 12C, an alignment device may comprise a light source 10, a collimator 15, a first beam splitter 31, a first light receiving module 25, a microprocessor 41, a power source 45, a memory 42, an alignment light emitter 17, an image beam splitter 33, an image sensor 53, and an actuator module 80. A spatial sensor is configured to detect the relative spatial position, movement, and inclination of the device and to assist better alignment of the alignment device. The spatial sensor may be an inertial sensor 52 to detect the acceleration or the inclination, a telemeter 55 to detect the distance between the optical measurement device and the analyte, or the combination to gather further spatial information. Here, the inertial sensor 52 may be an accelerometer or a gyroscope.

An alignment device may comprise a light source 10, a collimator 15, a first beam splitter 31, a second beam splitter 32, a first light receiving module 21, a second light receiving module 22, a microprocessor 41, a power source 45, a memory 42, and a spatial sensor.

Practically, the power intensity of light beams may dissipate along the traveling distance. In some examples, the measurement distance influences not only the alignment consistency but also the baseline reference of detected power intensity. Therefore, a baseline of power intensity correction is necessary for accurate measurement. People may appreciate that the optical measurement device may obtain the distance from the same region of an analyte as the measured region. An alignment device may comprise a light source 10, a collimator 15, a first beam splitter 31, a microprocessor 41, a power source 45, a memory 42, and a telemeter 55, which is configured to detect the distance between the analyte 99 and the device and to assist better alignment of the alignment device. Here, the telemeter 55 may be a fast-response photodetector coupled to the microprocessor 41 to calculate the distance by the time of flight between the light source 10 and the telemeter 55 or may be an interferometer to obtain the distance by interference.

In the example, an original light beam 110 becomes a collimated light beam 115 after passing through a collimator 15. A collimated light beam 115 may travels from a collimator 15 through the first beam splitter 31 reaching to an analyte 99. A first part of measurement light beam is delivered from the analyte 99 via the telemeter beam splitter 35 to the telemeter 55; a second part of measurement light beam is delivered from the analyte 99 via the telemeter beam splitter 35 to the second beam splitter 32 and then divided into a first detection light beam and a second detection light beam by the second beam splitter 32. A first detection light beam traveled from the second beam splitter 32 is detected by a first light receiving module 21, and a second detection light beam traveled from the second beam splitter 32 is detected by a second light receiving module 22.

An alignment device may comprise a light source 10, a collimator 15, a first beam splitter 31, a second beam splitter 32, a first light receiving module 21, a second light receiving module 22, a microprocessor 41, a power source 45, a memory 42, and an inertial sensor 52. An inertial sensor 52 is configured to detect the relative spatial position, movement, and inclination of the device and to assist better alignment of the alignment device. Here, the inertial sensor 52 may be an accelerometer or a gyroscope to detect the acceleration or the inclination of the alignment device.

Both telemeter 55 and inertial sensor 52 may provide extra spatial information to assist the alignment of the alignment device. In the example of manual alignment, the spatial information may be shown on the display 56 and indicate the user to achieve desired alignment. In the example of semi-automatic alignment, the alignment device may calculate the relative location between the alignment device and the analyte 99 according to the spatial information and the alignment information, so that it may show an indicator 118 assisting the user to correctly align the alignment device. Furthermore, the automatic alignment may be accomplished by controlling the actuator module 80 according to the spatial information and the alignment information.

An alignment device may comprise further comprise a housing. The housing is configured to facilitate the alignment process and to integrate all the components.

Figure 13A:
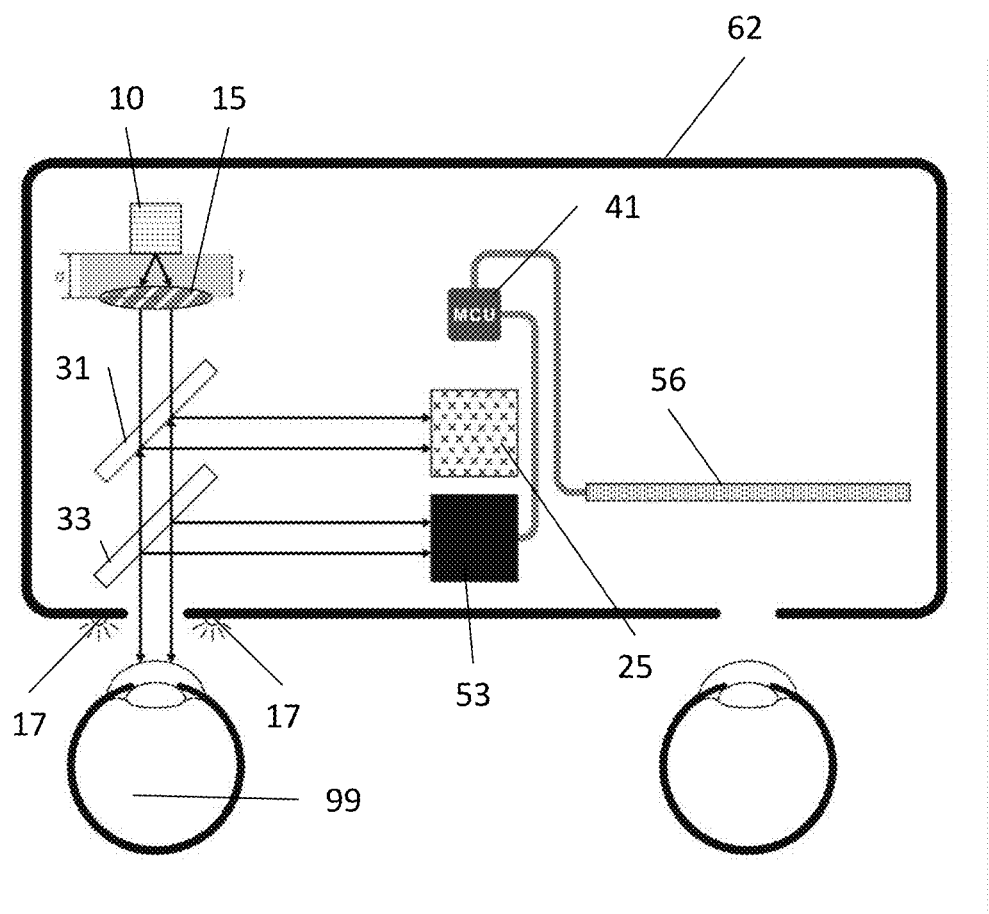
FIG. 13A is an example of an optical measurement device comprising a binocular housing.

In FIG. 13A, the housing is a binocular housing 62. A binocular housing 62 is configured to accommodate the components of the alignment device. The binocular housing 62 comprises a measurement window and an observation window. The measurement window is configured to allow the light path for the collimated light beam 115 and the measurement light beam. As well, the image sensor 53 may capture the image of the eye of interest and the alignment light spots 117 through the image beam splitter 33. The observation window is configured to allow the opposite eye to observe the display 56 showing the image information processed by the microprocessor 41.

Figure 13B:
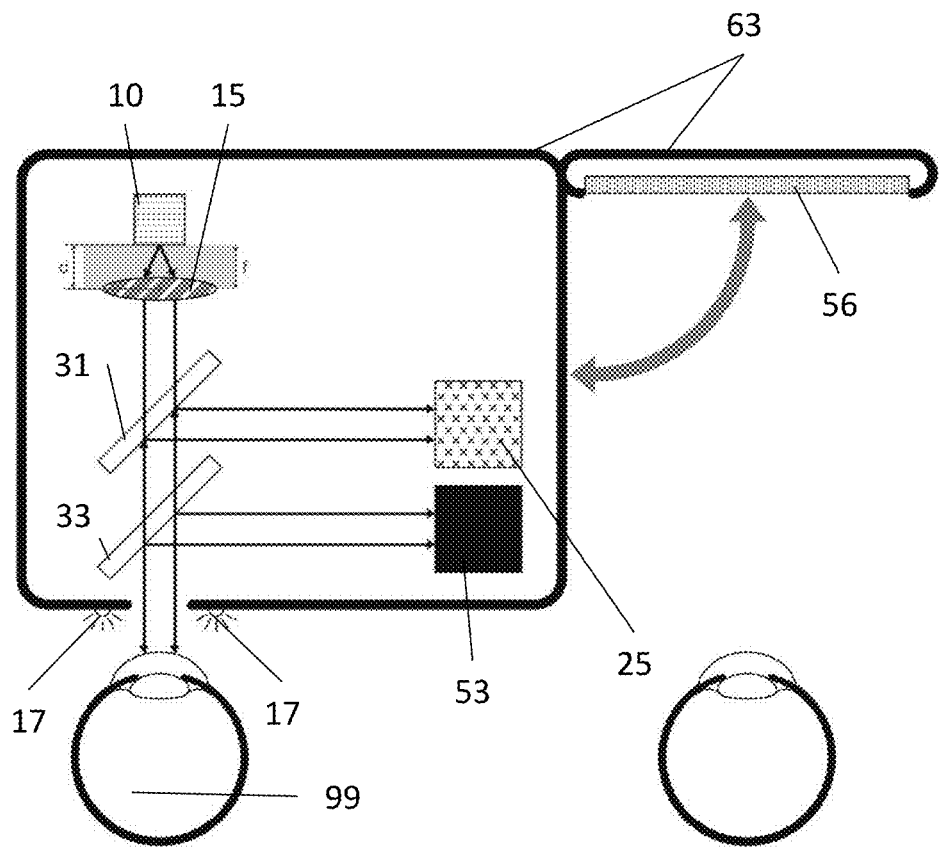
FIG. 13B is an example of an optical measurement device comprising a foldable housing.

In FIG. 13B, the housing is a foldable housing 63. A foldable housing 63, comprises a foldable frame and an ocular barrel. The foldable frame is configured to accommodate the display 56, and the ocular barrel is configured to accommodate the other components of the alignment device. The ocular barrel comprises a measurement window configured to allow the light path for the collimated light beam 115 and the measurement light beam. As well, the image sensor 53 may capture the image of the eye of interest and the alignment light spots 117 through the image beam splitter 33. The foldable frame is configured to accommodate the display 56 and allow the opposite eye to observe the display 56 showing the image information processed by the microprocessor 41.

Figure 13C:
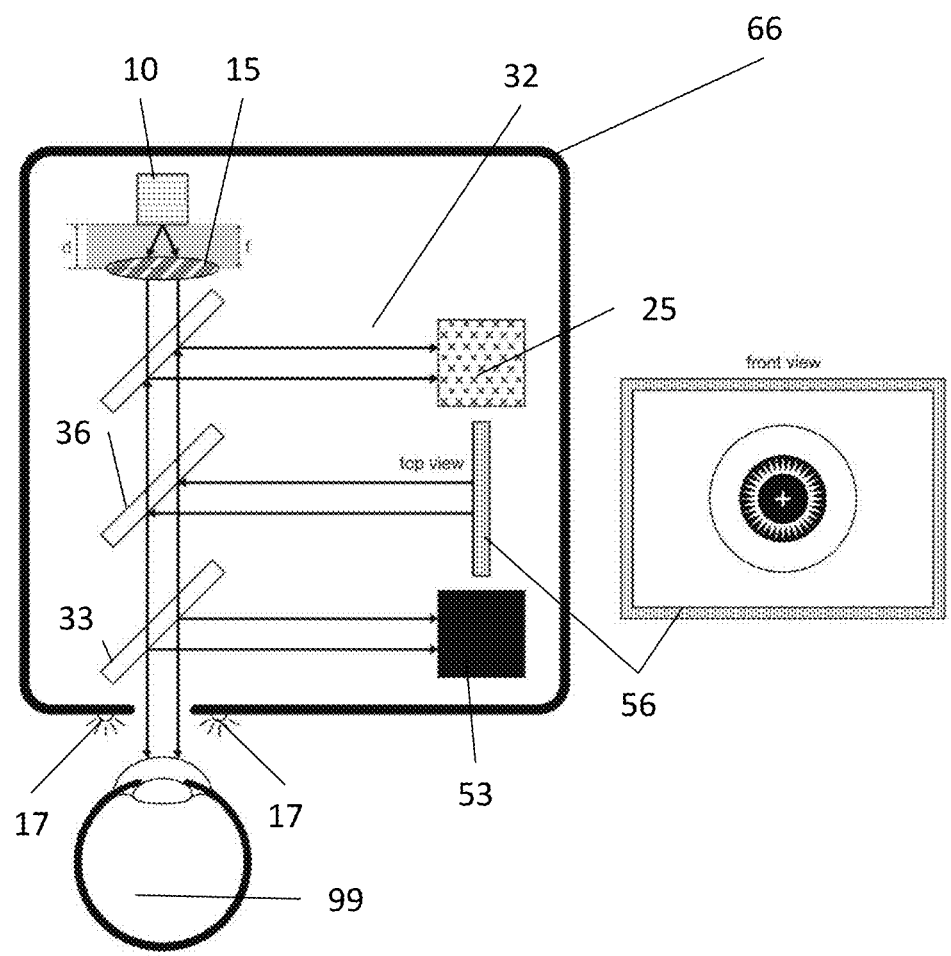
FIG. 13C is an example of an optical measurement device comprising a monocular housing.

In FIG. 13C, the alignment device further comprise a display beam splitter 36 and the housing is a monocular housing. A monocular housing 66 is configured to accommodate other components of the alignment device and facilitate self-measurement and alignment with single eye. The monocular handheld housing 66 also comprises a measurement window configured to allow the light path for the collimated light beam 115 and the measurement light beam. As well, the image sensor 53 may capture the image of the eye of interest and the alignment light spots 117 through the image beam splitter 33. The same eye of interest may observe the display 56 showing the image information projected on the display beam splitter 36.

At the age of present disclosure, the modules of the electronics, optoelectronics, optomechanics, and optics may be realized in compact size, so that the alignment device may be integrated as a part of a mobile device (for example, an optical measurement watch) or an accessory of the smart devices (for example, smart watches, smart phones, tablets, ultrabooks). The alignment device may be integrated as a part of the smart device and share the computing resources (e.g., MCU, storage media, communication modules), and the human interfaces (e.g., handheld housing, touch screen panel, virtual reality goggle, HUD helmet). It is contemplated that the alignment device may also be an appcessory, an accessory device connecting to a smart device via an app. Furthermore, the measurement data may be transmitted to a cloud server for big data or statistics applications.

Figure 14A:
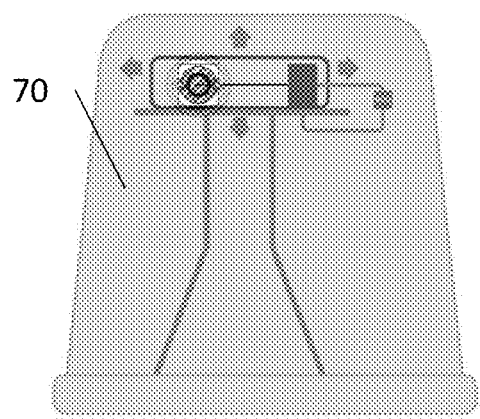
FIG. 14A is a side view of an example of an optical measurement device comprising a platform housing.
Figure 14B:
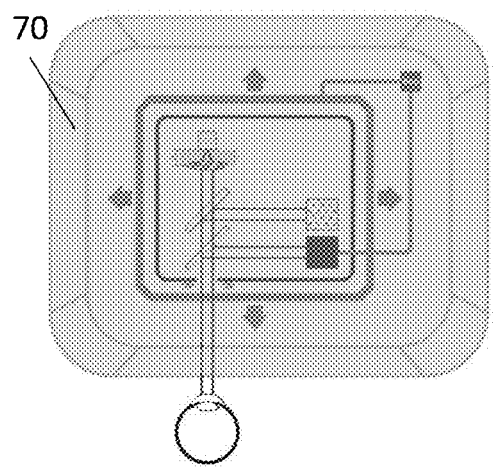
FIG. 14B is a top view of an example of an optical measurement device comprising a platform housing.

As, shown in FIG. 14A and FIG. 14B, an alignment device may further comprise a platform housing 70. The platform housing 70 comprises a connector module, a stand, and a housing. The connector module may provide mechanical connection and/or electrical connection between the alignment device and the platform housing 70. With mechanical connection, the alignment device is steadily fixed on the connector module, so that the spatial position and inclination can be initialized to the original status. Also, the connector module may provide electrical power and electrical signals to the alignment device through electrical connection. Moreover, the platform housing 70 may further comprise an actuator module 80 configured to assist alignment. In the examples, the user may control the actuator module 80 to align the alignment device or may control the actuator module 80 according to the indicator 118 showing on the display 56. In addition, the actuator module 80 may adjust the alignment according to the electrical signals sent out by the microprocessor 41 to achieve automatic alignment.

The examples shown and described above are only examples. Many details are often found in the art such as the other features. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, including in matters of shape and arrangement of the parts within the principles of the present disclosure up to, and including the full extent established by the broad general meaning of the terms used in the claims. It will therefore be appreciated that the examples described above may be modified within the scope of the claims.

What is claimed is:

1. An alignment device comprising:
   a light source that emits a reference light beam;
   an alignment light emitter that generates an alignment light spot on an analyte;
   an image beam splitter that directs the reference light beam to form a reference light spot on the analyte;
   an image sensor that captures an image of the analyte via the image beam splitter;
   a microprocessor that processes the image for alignment, and
   a memory that stores the image and a default alignment information,
   wherein the image comprises characteristics of the reference light spot, the alignment light spot and the analyte, and
   wherein the default alignment information comprises a reference light point, an alignment light point, and a landmark.

2. The alignment device according to claim 1, further comprising a housing that accommodates the light source, the alignment light emitter, the image sensor, the image beam splitter, the microprocessor, the memory.

3. The alignment device according to claim 2, wherein the housing is selected from the group consisting of a binocular housing, a foldable housing, a monocular housing and a platform housing.

4. The alignment device according to claim 1, further comprising a telemeter beam splitter and a telemeter, wherein the telemeter receives the reference light beam via the telemeter beam splitter.

5. The alignment device according to claim 1, further comprising a display connected to the microprocessor.

6. The alignment device according to claim 5, further comprising a display beam splitter that directs the image displayed on the display.

7. The alignment device according to claim 1, further comprising an actuator module configured to adjust the position of the alignment device according to the microprocessor.

8. The alignment device according to claim 1, further comprising a collimator that collimates the reference light beam into a collimated light beam.

9. The alignment device according to claim 1, further comprising a first beam splitter and a first light receiving module, wherein the first beam splitter directs a part of the reference light beam reflected from the analyte to the first light receiving module.

10. The alignment device according to claim 1, further comprising an inertial sensor.

11. An alignment method comprising:
    generating light spots on an analyte surface, wherein the light spots comprise an alignment light spot and a reference light spot;
    capturing an image comprising the reference light spot, the alignment light spot, and the analyte surface;
    displaying the image comprising a default alignment information, wherein the default alignment information comprises a reference light point, an alignment light point, and a landmark.

12. The alignment method according to claim 11, wherein the default alignment information is updated by the steps comprising:
    generating the light spots on the analyte surface, wherein the light spots comprise an alignment light spot and a reference light spot;
    capturing an image comprising the reference light spot, the alignment light spot, and the analyte surface;
    displaying the image comprising default alignment information, wherein the default alignment information comprises a reference light point, an alignment light point, and a landmark;
    receiving a confirmation signal from an user.

13. An alignment method comprising:
    generating light spots on an analyte surface, wherein the light spots comprise an alignment light spot and a reference light spot;
    capturing an image comprising the reference light spot, the alignment light spot, and the analyte surface;
    recognizing acquired alignment information comprising a reference light point, an alignment light point, and a landmark,
    determining the difference between the acquired alignment information and default alignment information, wherein the default alignment information comprises a reference light point, an alignment light point, and a landmark.

14. The alignment method according to claim 13, wherein the default alignment information is updated by the steps comprising:
    generating light spots comprising an alignment light spot and a reference light spot;
    capturing an image comprising a reference light spot, an alignment light spot, and an analyte;
    recognizing acquired alignment information comprising a reference light point, an alignment light point, and a landmark,
    displaying the image and default alignment information comprising a reference light point, an alignment light spot, and a landmark;
    receiving a confirmation signal from an user.

15. The alignment method according to claim 13, further comprising:
    displaying an indicator according to the difference between the acquired alignment information and the default alignment information.

16. The alignment method according to claim 13, further comprising:
    controlling an actuator module according to the difference between the acquired alignment information and the default alignment information.

17. The alignment method according to claim 13, further comprising:
    gathering spatial information detected by an inertial sensor or a telemeter.

18. The alignment method according to claim 17, further comprising:
    controlling an actuator module according to the spatial information.

* * * * *